(12) United States Patent
Pigott

(10) Patent No.: US 11,446,096 B2
(45) Date of Patent: Sep. 20, 2022

(54) MONITORING MEDICAL PROCEDURES BY ESTIMATED RADIATION EXPOSURE

(71) Applicant: John Pigott, Sylvania, OH (US)

(72) Inventor: John Pigott, Sylvania, OH (US)

( * ) Notice: Subject to any disclaimer, the term of this patent is extended or adjusted under 35 U.S.C. 154(b) by 0 days.

(21) Appl. No.: 17/314,568

(22) Filed: May 7, 2021

(65) Prior Publication Data

US 2021/0259786 A1 Aug. 26, 2021

Related U.S. Application Data

(63) Continuation-in-part of application No. 17/157,385, filed on Jan. 25, 2021, and a continuation-in-part of
(Continued)

(51) Int. Cl.
| | |
|---|---|
| *G01D 18/00* | (2006.01) |
| *A61B 34/20* | (2016.01) |
| *A61B 34/00* | (2016.01) |
| *A61B 90/00* | (2016.01) |
| *A61B 6/00* | (2006.01) |
| *G06N 20/00* | (2019.01) |

(52) U.S. Cl.
CPC .............. *A61B 34/20* (2016.02); *A61B 6/483* (2013.01); *A61B 34/25* (2016.02); *A61B 90/36* (2016.02);
(Continued)

(58) Field of Classification Search
CPC ......... A61B 34/20; A61B 6/483; A61B 34/25; A61B 90/36; A61B 2034/2059;
(Continued)

(56) References Cited

U.S. PATENT DOCUMENTS

| | | |
|---|---|---|
| 8,552,858 B2 | 10/2013 | Hohmann et al. |
| 8,774,361 B2 | 7/2014 | Kargar et al. |
| 2017/0220716 A1 | 8/2017 | Padoy et al. |

OTHER PUBLICATIONS

Alnewaini et al., "Real-time ray casting-based scatter dose estimation for c-arm x-ray system", Journal of Applied Clinical Medical Physics, vol. 18, No. 2, pp. 144-153. DOI:10.1002/acm2.12036 (Year: 2017).*

(Continued)

*Primary Examiner* — Kiho Kim
(74) *Attorney, Agent, or Firm* — Standley Law Group LLP; Adam J. Smith; Jeffrey S. Standley

(57) ABSTRACT

Systems and methods monitoring progress of a medical procedure by radiation exposure are provided. Locations of radiation producing and scattering items of medical equipment are received at a controller. Locations of individuals assisting with the medical procedure are received at the controller by way of tracking devices worn by the individuals during the medical procedure. The controller receives indication of when the radiation producing item(s) are activated and develops a radiation scatter intensity field. An analytical subsystem determines an estimated exposure level for each individual based on their position within the radiation scatter intensity field at each instance the radiation producing device is activated, which are compared to a benchmark. Where the estimated exposure level exceeds the benchmark, an intervention subsystem provides an intervention.

23 Claims, 19 Drawing Sheets
(9 of 19 Drawing Sheet(s) Filed in Color)

Related U.S. Application Data application No. 16/897,710, filed on Jun. 10, 2020, now Pat. No. 11,160,995, application No. 17/157,385, which is a continuation-in-part of application No. 16/897,710, filed on Jun. 10, 2020, now Pat. No. 11,160,995.

(60) Provisional application No. 62/859,935, filed on Jun. 11, 2019.

(52) U.S. Cl.
CPC ...... *G06N 20/00* (2019.01); *A61B 2034/2059* (2016.02); *A61B 2034/2074* (2016.02); *A61B 2034/256* (2016.02); *A61B 2090/365* (2016.02)

(58) Field of Classification Search
CPC ...... A61B 2034/2074; A61B 2034/256; A61B 2090/365; A61B 6/107; A61B 6/4441; A61B 6/547; A61B 2034/2048; A61B 2090/372; A61B 2090/376; A61B 2090/502; G06N 20/00; G01T 7/00; G01T 1/02; A61N 2005/1094; A61N 5/1075
See application file for complete search history.

(56) References Cited

OTHER PUBLICATIONS

Rodas, N., Seeing is believing: increasing intraoperative awareness to scattered radiation in interventional procedures by combining augmented reality, Montel Carlo simulations and wireless dosimeters, Int. J. Cars, pp. 1181-1191, 2015.

Fluke Biomedical, 05-106 and 01-104 Bleeper mR and Bleeper III Personal Radiation Monitors, Dec. 2013.

Mediview, Tech Overview, https://mediview.com/our-tech/, Accessed May 22, 2020.

VascularNews, Working with Radiation is Like Keeping a Pet Tiger in Your Living Room, Sep. 2015.

VascularNews, Radiation Exposure During EVAR Causes DNA Damage in Operators, https://vascularnews.com/radiation-exposure-evar-dna-damage-operators/, Oct. 27, 2017.

DI Cardiology, 5 Technologies to Reduce Cath Lab Radiation Exposure, https://www.dicardiology.com/article/5-technologies-reduce-cath-lab-radiation-exposure, Aug. 9, 2016.

American College of Cardiology, Highlights from SCAI2014 CardioSource, WoridNews Interventions, Real-Time Radiation Monitoring Reduces Exposure to Patients and Interventionalists, https://www.acc.org/latest-in-cardiology/articles/2014/05/22/14/43/highlights-from-scai-2014, Aug. 22, 2014.

Kirkwood, M et al.. Southern Association for Vascular Surgery, Surgeon Education Decreases Radiation Dose in Complex Endovascular Procedures and Improved Patient Safety, Sep. 2013, pp. 715-721, Volumbe 58, No. 3.

VascularNews, Alarming Lack of Physician Awareness About Radiation Hazards Exposed, Jun. 2014.

New England Society for Vascular Surgery, Defining the Radiation 'Scatter Cloud' in the Interventional Suite, Nov. 2013.

Rehn, E., Linkoping University, Modeling of Scatter Radiation During Interventional X-Ray Procedures, Jun. 2015.

\* cited by examiner

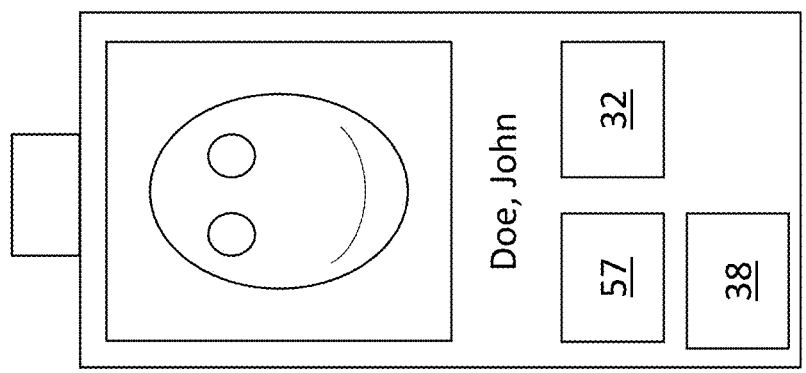
Figure 4

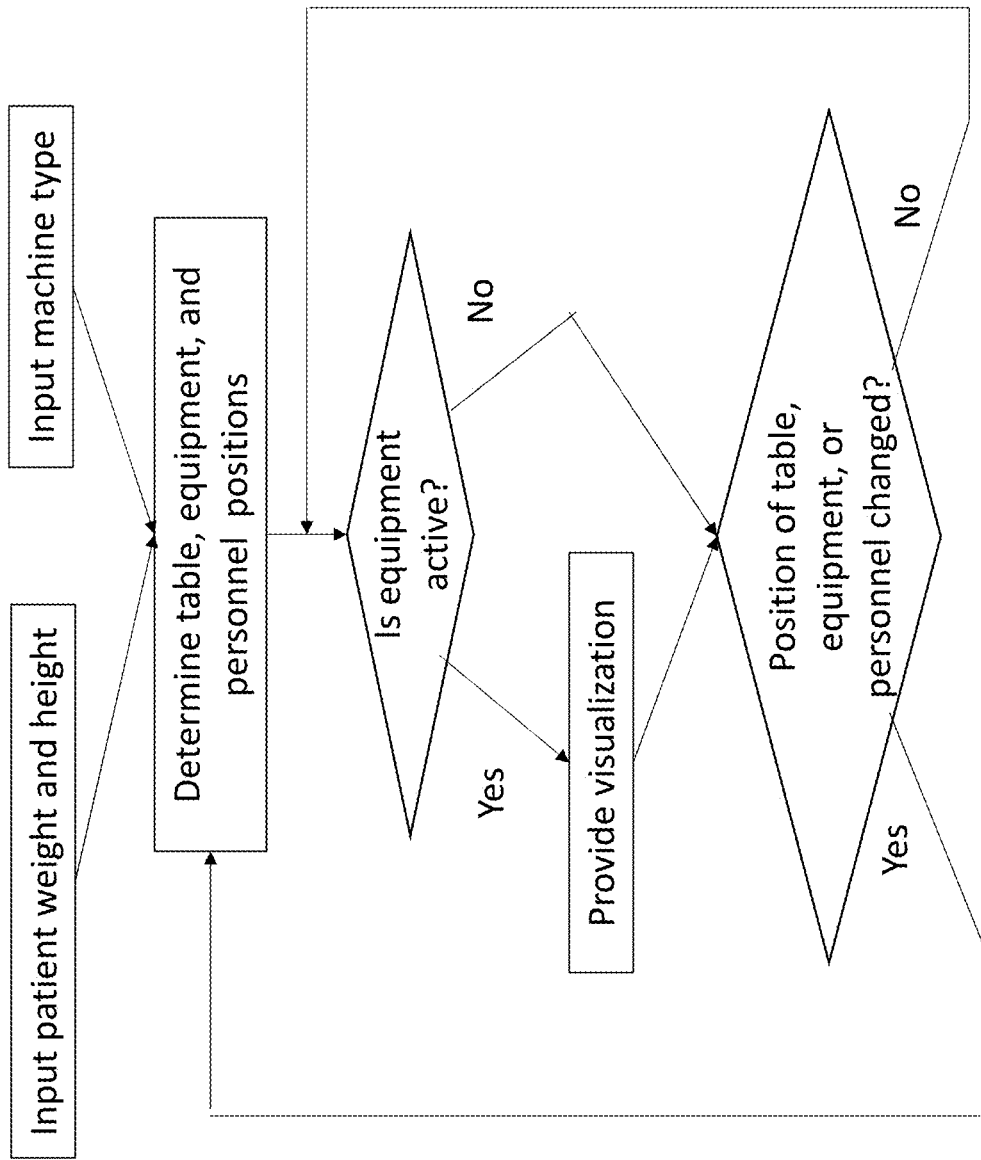

Profile
- Name
- Practice area
- Certifications/trainings
- Associated hospital/practice
- Years experience
- Age
- Average radiation exposure per procedure
- Cumulative radiation exposure last year
- All procedures performed
  - CPT/IDC code
  - Date/time
  - Radiation dosage
  - Patient information (age, weight, demographics, biometrics, lab information)
  - Equipment used
- Average procedures per year
- Number of procedures performed last year
- Predicted exposure for the year

MONITORING MEDICAL PROCEDURES BY ESTIMATED RADIATION EXPOSURE

CROSS-REFERENCE TO RELATED APPLICATIONS

This application is a continuation-in-part of U.S. application Ser. No. 17/157,385 filed Jan. 25, 2021, which is a continuation-in-part of U.S. application Ser. No. 16/897,710 filed Jun. 10, 2020, which claims the benefit of U.S. Provisional Application Ser. No. 62/859,935 filed Jun. 11, 2019. This application is also a continuation-in-part of U.S. application Ser. No. 16/897,710 filed Jun. 10, 2020, which claims the benefit of U.S. Provisional Application Ser. No. 62/859,935 filed Jun. 11, 2019. The disclosures of each of the foregoing are hereby incorporated by reference as if fully restated herein.

TECHNICAL FIELD

Exemplary embodiments relate generally to systems and methods for monitoring medical procedures by estimated radiation exposure.

BACKGROUND AND SUMMARY OF THE INVENTION

Many modern surgical procedures require the use of equipment which produces radiation. For example, to reduce the invasiveness of surgery, small devices are often used in conjunction with imaging equipment. A more specific example is vascular surgery, where small devices are inserted into a patient's vascular system and imaging equipment is used to track device position and blood flow. As radiation is released from such machines, it encounters the patient and other objects, such as the operating table, and may scatter through some or all of the operating room. Being invisible to the human eye, radiation exposure zones are difficult to track. Repeated or extended exposure to even minimal amounts of radiation can result in health risks to operating room staff. Radiation shielding and protective equipment, while helpful, do not altogether eliminate such exposures.

It is known to provide radiation tracking devices to medical personnel in an operating room to assist with tracking radiation exposure. These radiation tracking devices may be checked periodically, such as once a month, to determine approximate exposure levels over potentially multiple events of exposure in a given month. As a general rule, medical personnel are encouraged to stay at least six feet away from radiation producing equipment, when possible, to minimize exposure. However, it is difficult for medical personnel to constantly and accurately determine their distance from the equipment, especially in the course of an operation on a patient. Furthermore, radiation intensity varies based on a number of factors which change the radiation intensity for a given location. Medical personnel are able to make changes to their body positioning to reduce exposure if made aware of the location of the invisible and potentially harmful radiation. Therefore, what is needed is a system and method for visualizing scattered radiation in a medical facility.

Systems and methods for visualization of scattered radiation in a medical facility are disclosed. The medical facility may comprise an operating room, for example, though the systems and methods may be used with other medical facilities such as but not limited to, training environments, simulators, laboratories (e.g., catheterization labs), radiology suites, imagining scanner rooms (e.g., CT scanners, MRI scanners), combinations thereof, or the like. The medical facility may comprise one or more items of medical equipment configured to produce radiation for medical reasons such as, but not limited to, treatment and/or diagnosis of diseases. Examples of such equipment which produces radiation includes, but is not necessarily limited to, imaging equipment (e.g., CT scanners, MRI machines, X-RAY machines, electron microscopes, fluoroscopy equipment, combinations thereof, or the like), radiation therapy machines (e.g., external beam radiation machines, sealed source radiation therapy machines, unsealed source radiotherapy machines, photon therapy machines, oncology equipment, combinations thereof, or the like), accelerators, or other equipment capable of producing radiation for medical treatment purposes, that in high enough levels of repeated exposure could be harmful to humans.

Alternatively, or additionally, the medical facility may comprise radioactive medical products and/or medical products which naturally produce radiation, or are configured to produce radiation for medical reasons, such as but not limited to, the treatment and diagnosis of diseases. Examples of such products include, but are not limited to, various isotypes, radiopaque markers, fluoroscopy fluids, seeds, combinations thereof, or the like.

These items of equipment and/or products may be configured to deliberately produce what is considered to be safe or otherwise medically acceptable levels of exposure to radiation for patients, for their medical care. Examples of such radiation include, but are not necessarily limited to, gamma rays, x-rays, charged particles, combinations thereof, or the like. While generally safe or otherwise medically acceptable levels of radiation exposure to patients having a given medical procedure is one thing, repeated levels of radiation exposure to medical personnel who conduct multiple medical procedures over multiple patients, is another. For example, medical science generally accepts a safe or medically acceptable level of radiation exposure for patients, but exposure to that same level and amount of radiation by a medical professional over a long career may be of more concern.

Information may be provided regarding, for example without limitation, a type of radiation producing medical equipment device, patient height, and patient weight. The position of one or more items of equipment in the medical facility may be determined from one or more position sensors. The equipment may include radiation producing equipment. Alternatively, or additionally, the equipment may include medical equipment which scatters radiation, deliberately or unintentionally, when placed in the path of the same. Examples of such equipment which scatters radiation include an operating table, trays, cabinetry, medical devices, combinations thereof, or the like. The operating table is a common source of radiation scatter as it is often placed directly in the path of a radiation beam and comprises one or more metals which scatter encountered radiation.

A visualization of the radiation scatter may be generated by a controller and provided at one or more visualization devices. The visualization devices may include augmented reality ("AR") tracking devices, electronic displays, and/or projection devices.

The visualization may be configured to appear fixed relative to the various visualization devices such that as medical personnel move about the medical facility and/or change their gaze, the visualization is updated at their visualization device to appear to be in the same location. The location may comprise, for example without limitation, adjacent to or at radiation producing equipment, equipment which scatters radiation, the patient, the operating table, combinations thereof, or the like. As the position of the operating table, the patient, equipment which produces radiation, equipment which scatters radiation, and/or other equipment and/or medical personnel in the medical facility is changed, the visualization may be updated.

Each medical personnel in the medical facility may be outfitted with a position tracking device. Alternatively, or additionally, various pieces of equipment in the medical facility, such as but not limited to, the operating table, radiation producing equipment, storage equipment, trays, radiation producing products, medical devices, equipment which scatters radiation, and the like may be outfitted with position tracking devices. In this way, the position of such people and/or items may be tracked for updating the visualization. Multiple position devices may be utilized for a given person or piece of equipment. Updates to the visualization may be made in substantially real time.

The visualization may comprise a multi-layered cloud or sphere, though other forms such as, but not limited to, lines, shapes, text, color, or the like may be utilized in the alternative or in addition. Various areas of the visualization may be color coded, shape coded, marked with text, provided in certain densities or intensities, some combination thereof, or the like to indicate the danger level associated with expected radiation intensity for that area. In another exemplary embodiment, a single light may be increased in intensity or illuminance to indicate relatively higher relative radiation. Alternatively, or additionally, sounds may be emitted in varying tone, frequencies, amplitudes, some combination thereof, or the like as the personnel approach radiation producing equipment. Regardless, the visualization and/or audio feedback may provide medical personnel in the medical facility with real time, qualitative type feedback regarding their expected level of danger. Medical personnel may use this feedback to limit their exposure level.

The visualization may be provided at a transparency level sufficient to permit the personnel to see the patient and equipment in the room while also viewing the visualization. By way of non-limiting example, transparency levels of 20% or under may be utilized.

In exemplary embodiments, at least some of the visualization devices may comprise radiation exposure tracking devices. Exposure data from such devices may be used to improve the accuracy of the visualization and/or track personnel exposure levels. Alternatively, or additionally, relative exposure may be tracked by position of the personnel while the radiation producing equipment is active. Regardless, exposures data may be recorded to calculate various exposure levels over time, predicted exposure levels, average exposure levels, some combination thereof or the like. Such data may be generated into one or more reports and/or provided as alerts, such as when a person approaches a periodic goal or threshold.

In other exemplary embodiments, the medical facility may comprise one or more training facilities and/or simulators. In such cases, some or all of the medical equipment in the medical facility, such as but not limited to the radiation producing equipment, radioactive products, equipment which scatters radiation, and/or other medical equipment may be simulated or real. The radiation emitted by such equipment and/or products and/or scattered by other such equipment may be simulated and the visualization may be provided to simulate such radiation. This may be used to raise awareness of radiation exposure, train personnel, evaluate the impact of procedures on radiation exposure, test new procedures, combinations thereof, or the like.

It will be appreciated by those of skill in the art that the systems and/or methods shown and/or described herein may be used in conjunction with any type of healthcare setting, with any type of equipment and/or to visualize any type of radiation. The types of radiation may be those defined by the Occupational Safety and Health Administration, Nuclear Regulatory Commission, Centers for Disease Control, the Food and Drug Administration, or other governmental or regulatory body, standards setting organization, combinations thereof, or the like, that in high enough levels and/or amounts of exposure is deemed to be harmful to humans. For example, without limitation, such radiation may include the types or kinds of radiation that in high enough levels of exposure is known to increase the incidence of cancer in humans following such exposure.

Judging complexity and progress of a medical procedure (hereinafter also a "case") is a difficult and uncertain endeavor. This is particularly unfortunate considering that case complexity and progress are important measures of patient outcome as well as operator and other personnel performance. Therefore, what is needed are systems and methods for monitoring case complexity and progress.

System and methods for monitoring progress and complexity of a medical procedure, such as by tracking estimated radiation exposure are provided. Radiation exposure may serve as an effective surrogate for case progress and complexity. More complex cases tend to require additional imaging, operating time, and/or physical proximity to radiation producing and/or scattering equipment (which is typically physically proximate to the patient) for the operator or other personnel relative to less complex cases. Thus, more complex cases, or even portions of cases, may tend to result in increased radiation exposure relative to other, less complex cases, or portions of cases. Alternatively, or additionally, as a case progresses, radiation exposure may increase. For example, without limitation, multiple imagining sessions may be performed during the course of a procedure and/or the operator or other personnel may spend more time physically proximate to radiation producing or scattering devices as a case proceeds. Thus, radiation exposure may increase as a case is performed.

Radiation exposure levels during a case may be estimated using the tracking devices, with or without the scattered radiation visualization. Where tracking devices worn by various personnel for a procedure report a location within a radiation scatter area while radiation production is underway, the controller may record an estimated radiation exposure amount for the individual(s). Alternatively, or additionally, the radiation exposure measurement devices may be utilized.

Estimated radiation exposure may be tracked, such as by multiple individuals over multiple procedures at multiple medical facilities, to develop a database of estimated radiation exposure for various medical procedures. Such radiation exposure may be associated with personnel information regarding the individual wearing or otherwise associated with the tracking device and/or with patient information. For example, information about personnel may include demographic information, education, training, and/or certification information, associated medical facilities, combinations thereof, and the like. Such estimated radiation exposures may, alternatively or additionally, be associated with information about the procedure performed, such as but not limited to, medical codes, date and time information, devices used, combinations thereof, or the like. This information may be analyzed to develop averages, medians, ranges or other benchmarks. The benchmarks may be specific to the type or kind of procedure performed (e.g., by CPT or IDC code), the personnel or certain personnel information (e.g., experience, training, education, etc.), a medical facility or geographic area, patient demographics (e.g., age, co-morbidities, risk factors, etc.), combinations thereof, or the like.

After further cases are performed, or while such further cases are underway, radiation exposure levels (estimated and/or actual) may be tracked and compared to such benchmarks to identify the need for intervention. For example, where a tracked radiation exposure level is found to exceed a benchmark by more than a predetermined amount, an intervention may be triggered. Such benchmarks may be developed automatically, on demand, combinations thereof, or the like. Machine learning, artificial intelligence, and/or statistical analysis techniques (e.g., averages, weighted averages, median, mode, standard deviations, etc.) may be utilized to develop such benchmarks.

Interventions may include, for example without limitation, identifying candidates for additional training and/or education, providing such training and/or education, providing access to medical literature and/or training materials, videoconferencing or teleconferencing access to other medical personnel (e.g., a more experienced operator) or other relevant parties (e.g., technical support staff), access to a chatbot or artificial intelligence entity, auditory or visual feedback, notifications information, information regarding new devices or techniques available to improve efficiency and/or reduce exposure, combinations thereof, or the like. Such interventions may be provided in substantially real-time, such as during the procedure, or after, such as but not limited to, in a post-operative review, during quarterly, annual, etc. review, combinations thereof or the like. Particularly where the interventions are provided while a procedure is underway, such interventions may be provided by way of the AR tracking devices in an augmented reality fashion. Interventions may be provided directly to the personnel or to other associated parties such as hospital or other medical practice administrators, medical device companies, insurance providers, combinations thereof, or the like, to name a few examples without limitation.

While some discussion is made herein with regards to medical applications, those of skill in the art will recognize that applications in other radiation environments may be realized. For example, without limitation, such radiation producing environments may include security screening areas which utilize radiation producing equipment, nuclear power facilities, nuclear production facilities, combinations thereof, or the like.

Further features and advantages of the systems and methods disclosed herein, as well as the structure and operation of various aspects of the present disclosure, are described in detail below with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee. In addition to the features mentioned above, other aspects of the present invention will be readily apparent from the following descriptions of the drawings and exemplary embodiments, wherein like reference numerals across the several views refer to identical or equivalent features, and wherein:

FIG. 4 is a front view of an exemplary tracking device in accordance with the present invention;

FIG. 14 is a flow chart with exemplary logic for operating the various visualization systems in accordance with the present invention;

FIG. 18 is a plan view of an exemplary profile generated by the system of FIG. 17.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
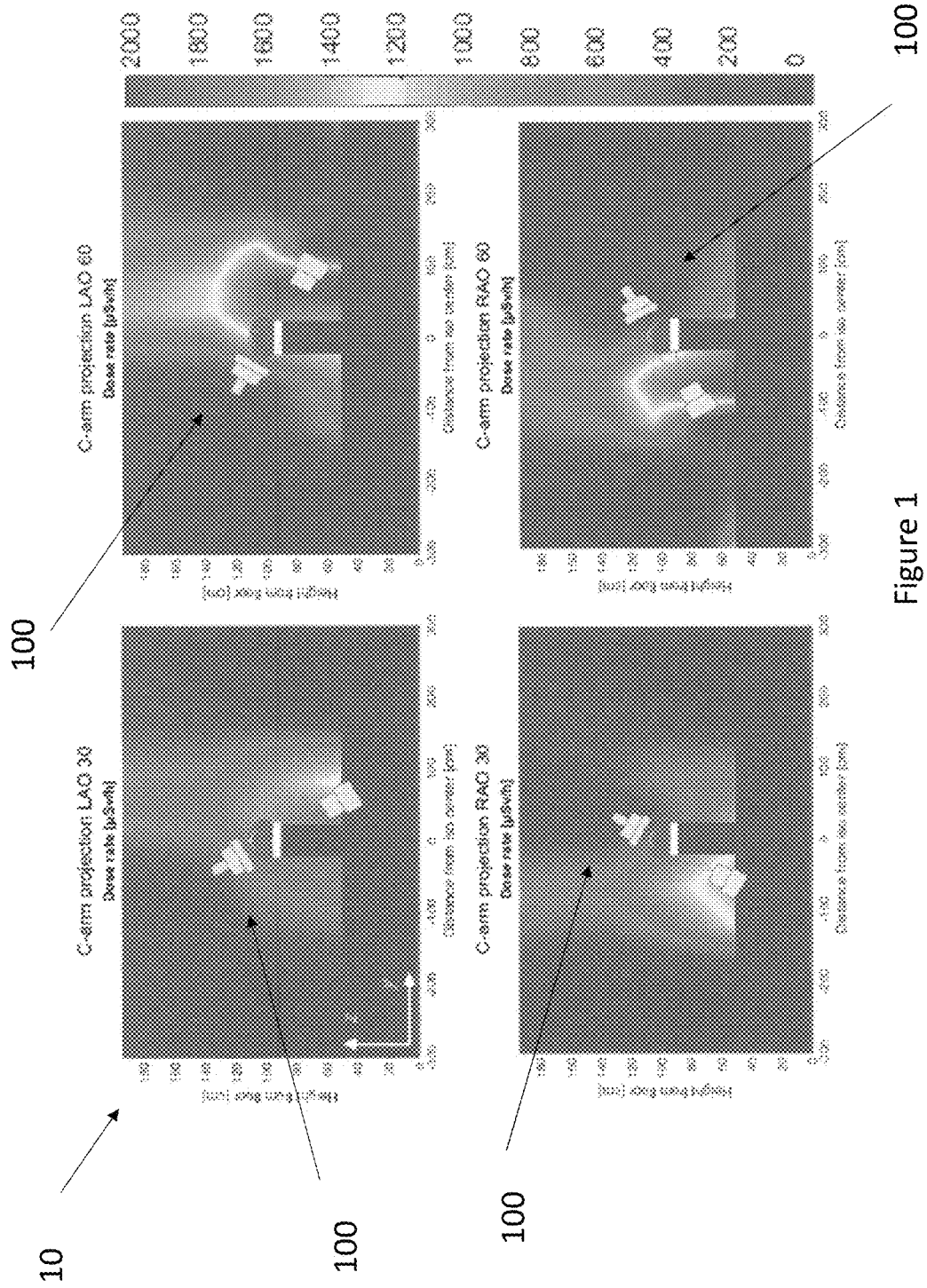
FIG. 1 is a plan view of an exemplary conventional, two-dimensional radiation scatter intensity diagram.
Figure 2:
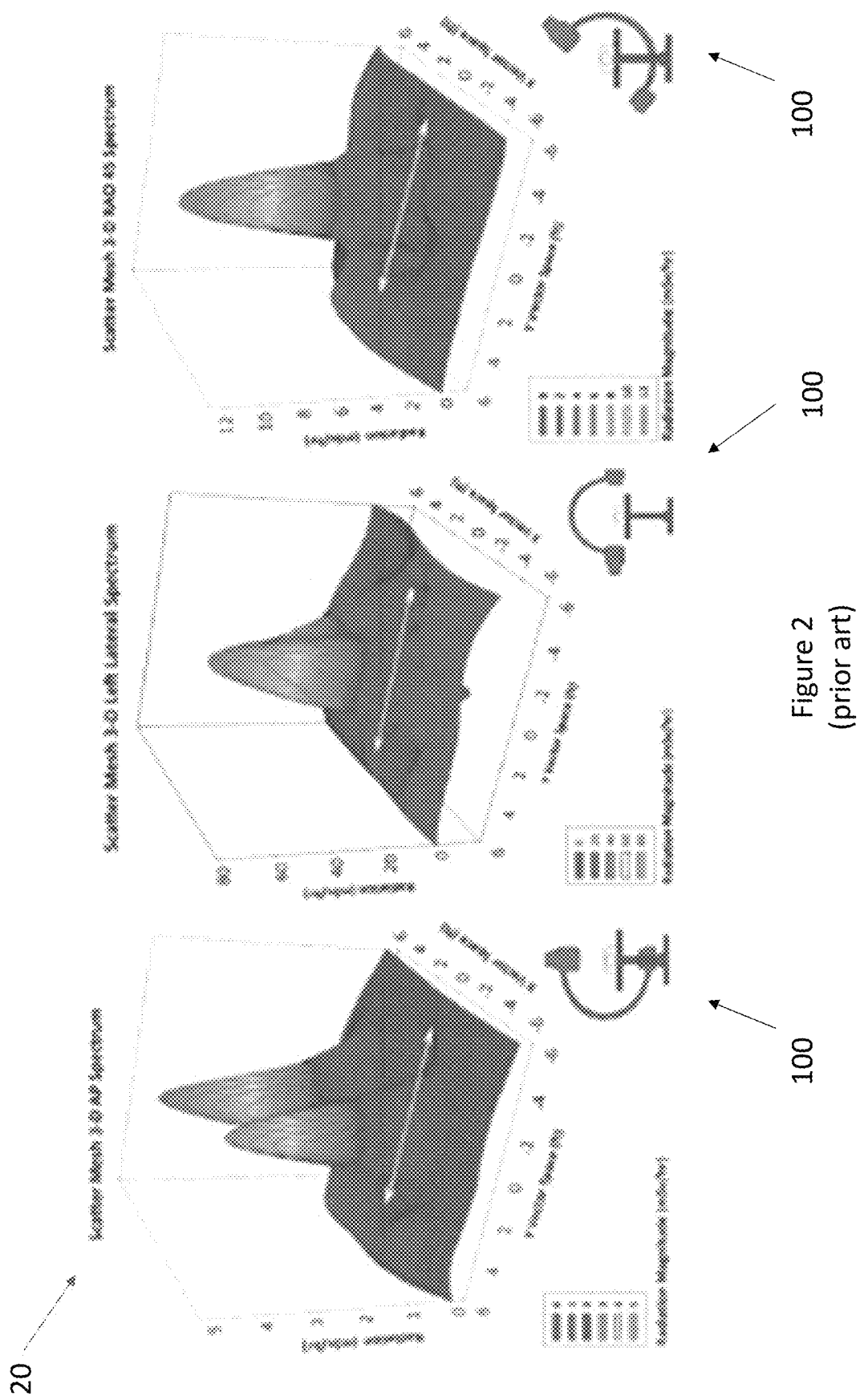
FIG. 2 is a perspective view of an exemplary conventional, three-dimensional radiation scatter intensity diagram.

FIG. 1 illustrates an exemplary, conventional two-dimensional radiation scatter intensity diagram 10. FIG. 2 illustrates an exemplary, conventional three-dimensional radiation intensity diagram 20. Such diagrams 10, 20 may be provided by manufacturers of radiation producing medical equipment 100 or other sources. The equipment 100 may comprise, without limitation, one or more imaging devices. The diagrams 10, 20 may be specific to the type, brand, make, model, some combination thereof, or the like of the equipment 100. Multiple diagrams may be provided for various orientations, settings, some combination thereof, or the like of the equipment 100. The diagrams 10, 20 may be color coded to reflect the radiation intensity of a given area.

Figure 3:
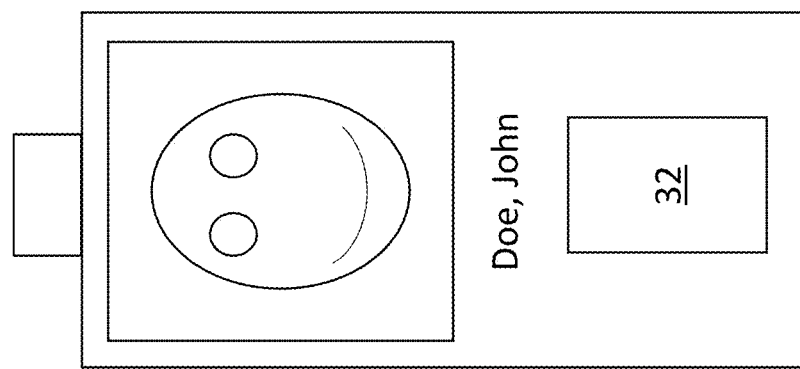
FIG. 3 is a front view an exemplary conventional radiation exposure tracking device.

FIG. 3 illustrates an exemplary, conventional radiation tracking device 30. Typically, such devices 30 are provided as badges which may comprise identifying information such as photos, names, some combination thereof, or the like. The device 30 may comprise a radiation exposure measurement device 32. The radiation exposure measurement device 32 may comprise, for example without limitation, a dosimeter, Geiger counter, alpha radiation survey meter, dose rate meter, some combination thereof, or the like. Such devices 30 may be worn by personnel, such as when in a medical facility. The devices 30 may be periodically checked, such as once a month, to determine radiation exposure.

FIG. 4 illustrates an exemplary tracking device 36. The tracking device 36 may comprise one or more of the radiation exposure measurement devices 32, though such is not required. The tracking device 36 may comprise one or more position tracking devices 57 configured to track the location and/or orientation of the tracking device 36. The position tracking devices 57 may comprise a GPS device, wi-fi device, near field communication device, accelerometer, gyroscope, angle sensor, magnetometer, some combination thereof, or the like. In this way, the location and/or radiation exposure of the personnel wearing the tracking device 36 may be monitored. The tracking device 36 may comprise a network connectivity device 38 configured to place the tracking device 36 in communication with one or more remote devices, such as but not limited to, a controller 56. Data regarding location and/or radiation exposure may be transmitted to the controller 56 by way of the network connectivity device 38. The location and/or radiation exposure may be monitored and/or transmitted continuously or periodically.

In other exemplary embodiments, the tracking devices 36 may comprise the position tracking device 57 and/or the network connectivity device 38, but not the radiation exposure measurement device 32.

A number of tracking devices 36 and/or radiation tracking devices 30 may be utilized on each person in the medical facility in accordance with the present invention. In exemplary embodiments, without limitation, each person in the medical facility may be outfitted with tracking devices 36 and/or radiation tracking devices 30 on different parts of their body. For example, without limitation, such devices 36, 30 may be positioned at the person's head, neck, torso, wrists, ankles, arms, legs, some combination thereof or the like to measure the position and/or radiation exposure of these individual parts of the person's body. Often, a particular area of the person may be exposed to a different level of relative radiation for a different period of time than other areas of the person's body. For example, without limitation, a surgeon's hands and/or eyes may be exposed to higher levels of relative radiation for longer periods of time as the surgeon may be unable to move his or her hands when performing a procedure. By using multiple tracking devices 32, distance from the equipment 100, relative exposure levels, and other data specific to certain parts of the body may be determined and/or tracked.

Distance, relative exposure levels, and other data may be tracked and/or reported in real time or may be stored for post-operative review. For example, without limitation, distance from the equipment 100, location, relative exposure levels, and other data may be monitored and/or reported in real time, post-operative, every few seconds, some combination thereof, or the like. By way of a non-limiting example, as used herein the term real time or substantially real time may account for transmission times, temporary storage times, data processing times, lag times, some combination thereof, or the like.

Figure 5:
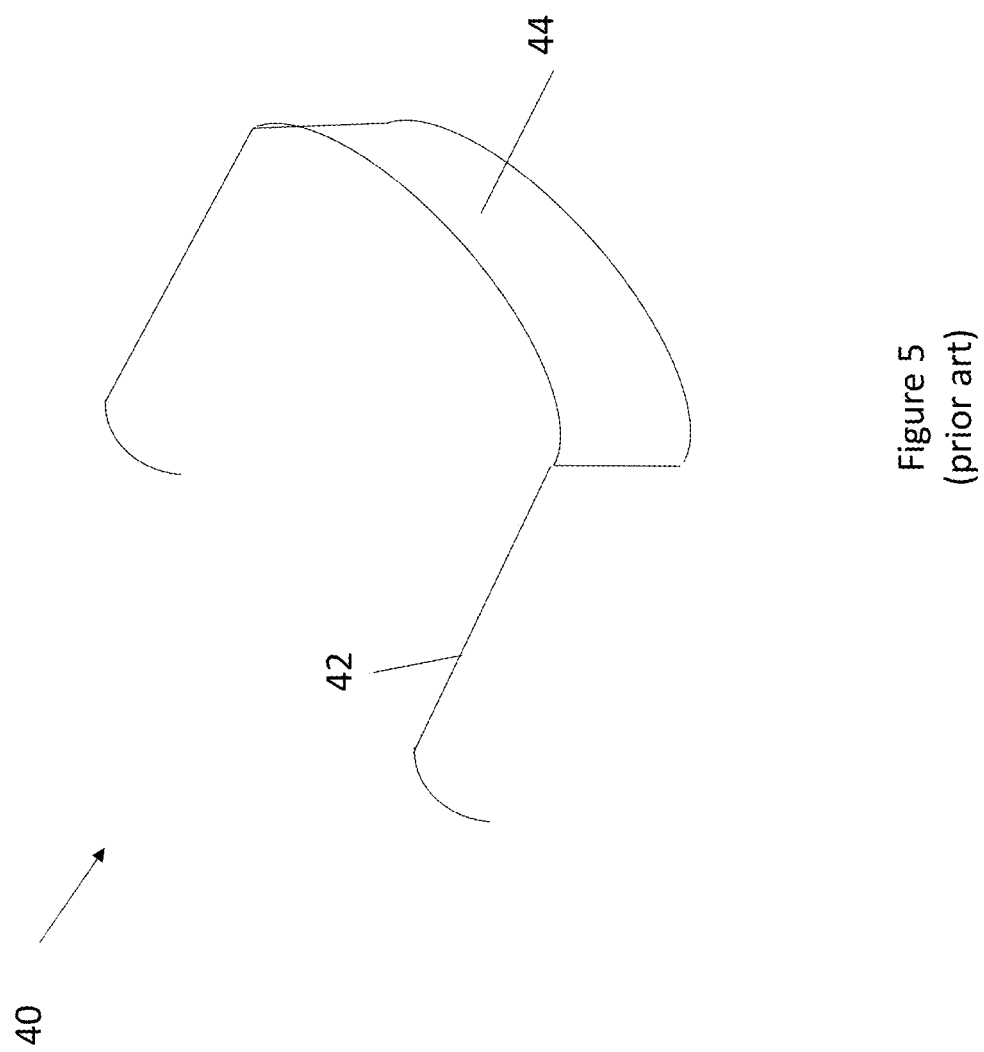
FIG. 5 is a perspective view of an exemplary conventional augmented reality device.

FIG. 5 illustrates an exemplary, conventional augmented reality ("AR") device 40. The AR device 40 may comprise one or more body attachment portions 42. The body attachment portions 42 may comprise head bands, frames, contact lenses, some combination thereof, or the like. The AR device 40 may comprise one or more display portions 44. The display portion 44 may comprise a transparent or translucent material. The display portions 44 may be configured to display one or more images. The display portions 44 may comprise one or more screens, shields, glasses, display surfaces, contact lenses, glasses lenses, some combination thereof, or the like. Examples of such AR devices 40 include, but are not limited to, Glass® from Google® (https://www.google.com/glass/start/), HoloLens® from Microsoft® (https://www.microsoft.com/en-us/hololens). The display portion 44 may be configured to display images in a way which permits the user to see the real world beyond the display portion 44 such that the images are overlaid onto the real world.

Figure 6:
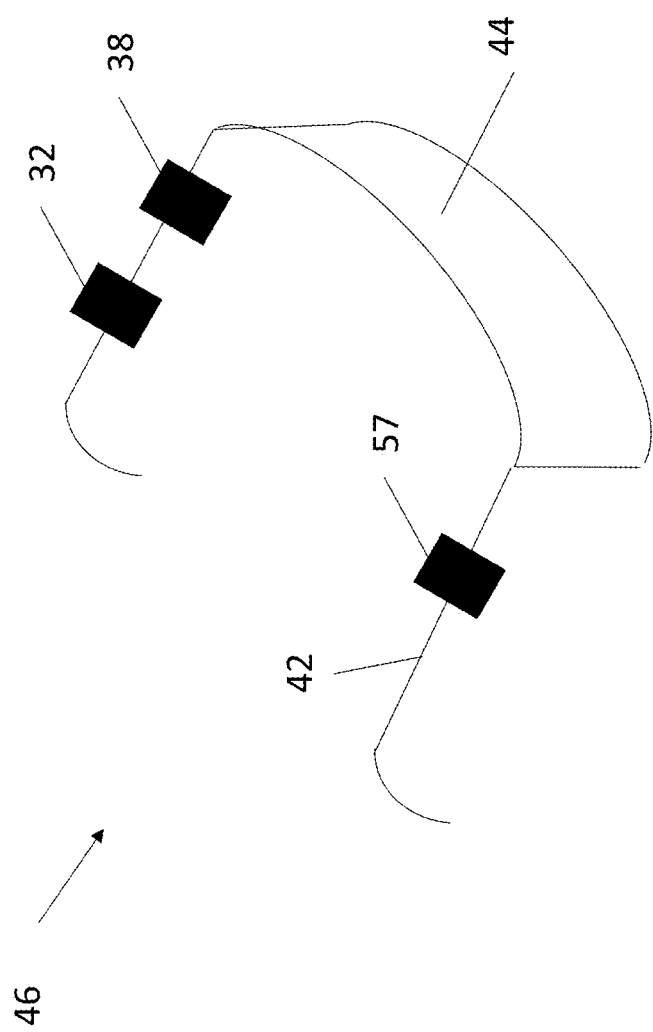
FIG. 6 is a perspective view of an exemplary augmented reality tracking device in accordance with the present invention.
Figure 7:
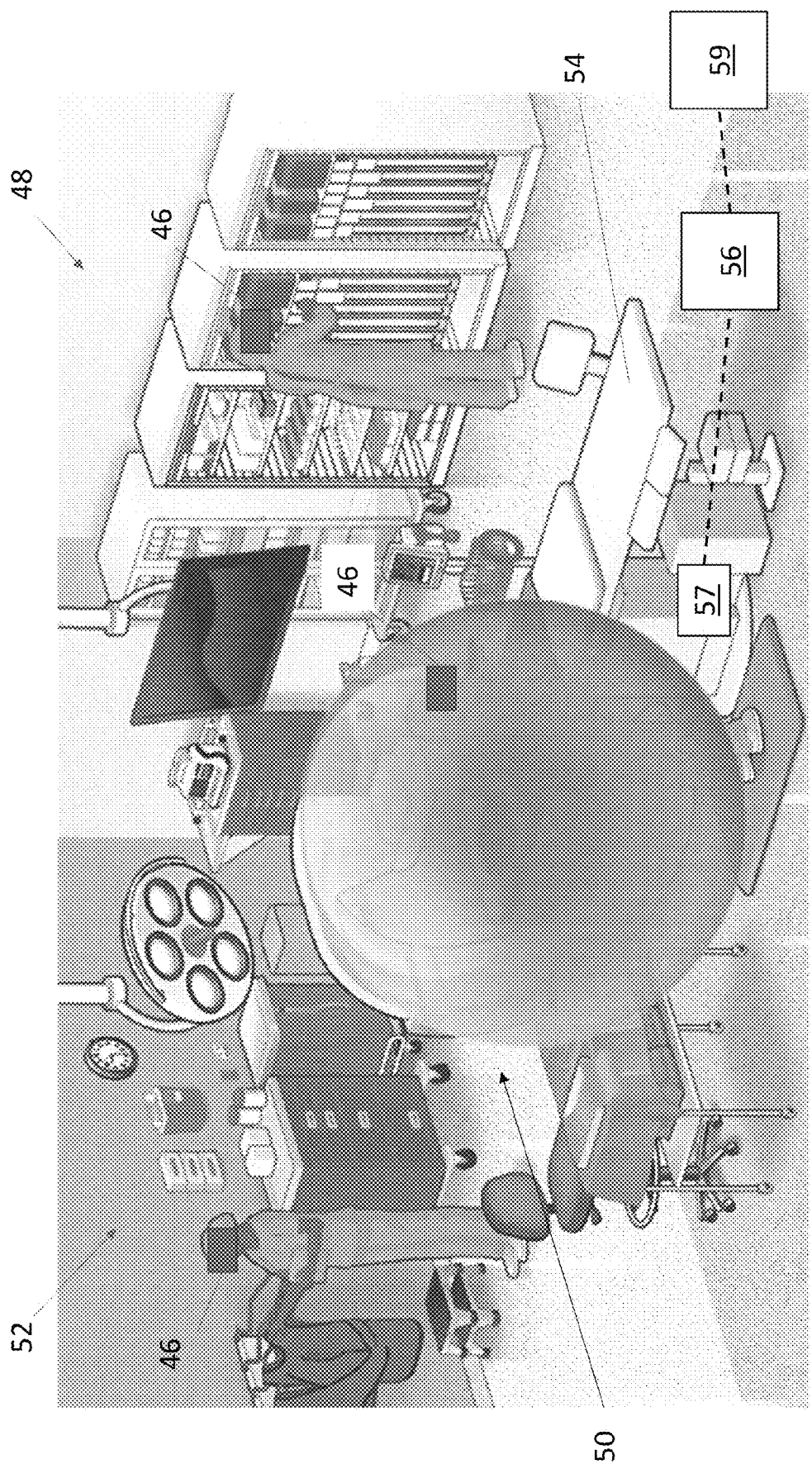
FIG. 7 is a perspective view of a medical facility with an exemplary radiation scatter visualization using an exemplary augmented reality system in accordance with the present invention.
Figure 8:
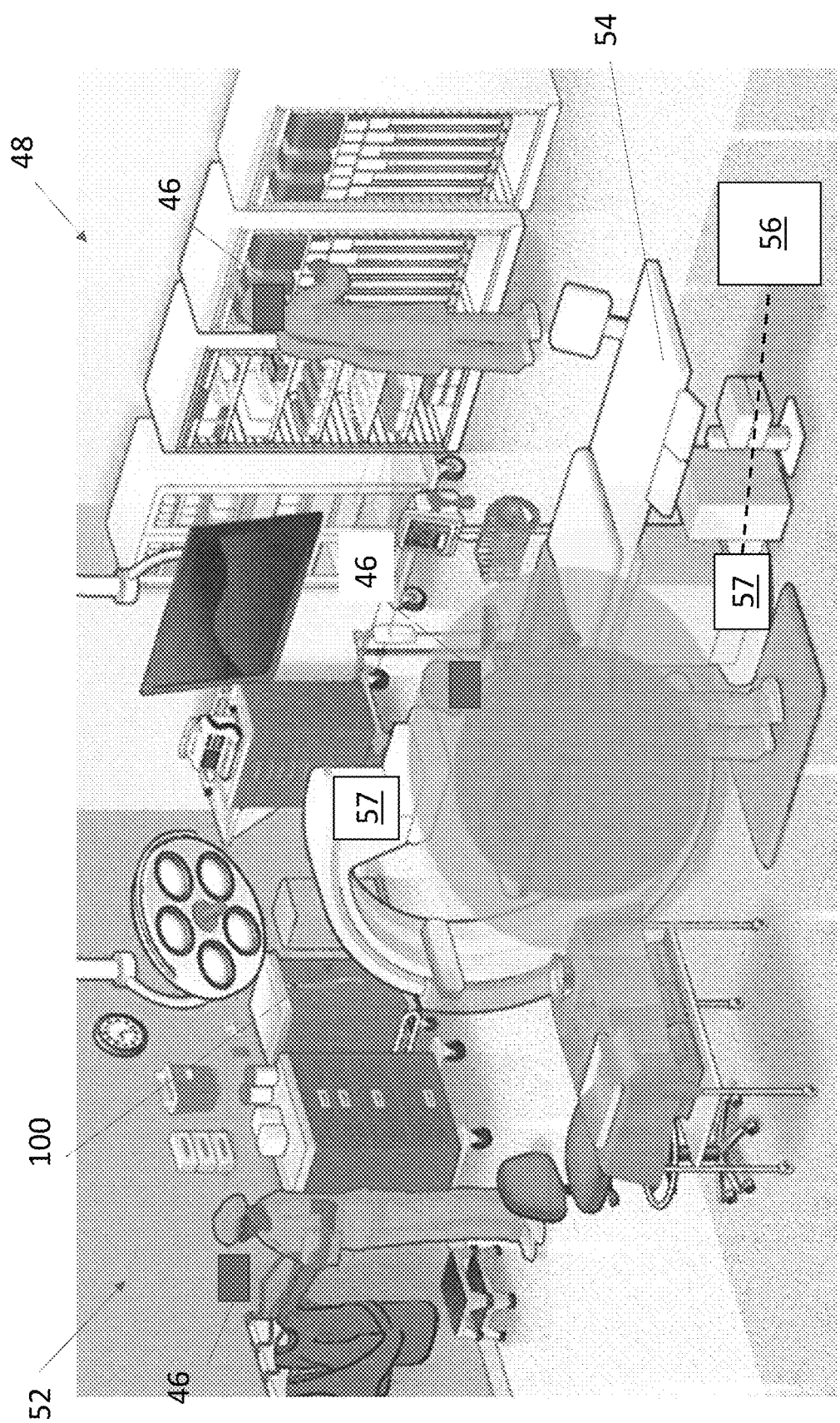
FIG. 8 is a perspective view of the medical facility of FIG. 7 with another exemplary radiation scatter visualization.

FIG. 6 illustrates an exemplary AR tracking device 46. The AR tracking device 46 may comprise the radiation exposure measurement device 32. The AR tracking device 46 may, alternatively or additionally, comprise one or more position tracking device 57 configured to track the location and/or orientation of the AR tracking device 46. In exemplary embodiments, the position tracking device 57 may be configured to track the orientation of the user's head, and therefore their gaze. In this way, the AR tracking device 46 may be configured to track the location and/or radiation exposure of personnel wearing the AR tracking device 46 while providing visual images to said person.

The AR tracking device 46 may comprise the network connectivity device 38. The location and/or radiation exposure may be monitored and/or transmitted continuously or periodically to remote devices, such as but not limited to, the controller 56.

FIG. 7 through FIG. 10 illustrates exemplary medical facility 52 with exemplary augmented reality system 48. The medical facility 52 may comprise an operating room, for example, though the augmented reality system 48 may be utilized in association with other types of medical facilities 52 may be utilized such as but not limited to, training environments, simulators, laboratories (e.g., catheterization labs), radiology suites, imagining scanner rooms (e.g., CT scanners, MRI scanners), combinations thereof, or the like.

The medical facility 52 may comprise one or more items of medical equipment 100 configured to produce radiation for medical purposes, such as but not limited to, the treatment and/or diagnosis of disease. Such radiation producing medical equipment 100 may comprise, for example without limitation, imagining equipment (e.g., CT scanners, MRI machines, X-RAY machines, electron microscopes, fluoroscopy equipment, combinations thereof, or the like), radiation machines (e.g., external beam radiation machines, sealed source radiation therapy machines, unsealed source radiotherapy machines, photon therapy machines, oncology equipment, combinations thereof, or the like), accelerators, or other equipment capable of producing radiation for medical care purposes, such as but not limited to, gamma rays, x-rays, charged particles, combinations thereof, or the like. Alternatively, or additionally, the medical facility 52 may comprise one or more radioactive medical products and/or products capable of producing radiation for medical purposes, such as but not limited to, the treatment and/or diagnosis of disease. Such products may include, for example without imitation, various isotypes, radiopaque markers, fluoroscopy fluids, seeds, combinations thereof, or the like which produce radiation.

The medical facility 52 may comprise, alternatively or additionally, medical equipment which scatters radiation 54, deliberately or unintentionally, when placed in the path of such radiation. Examples of such equipment which scatters radiation 54 includes, but is not limited to, operating tables, trays, cabinetry, medical devices, metallic surfaces, shielding, combinations thereof, or the like. The operating table is a common source of radiation scatter as it is often placed directly in the path of a radiation beam and comprises one or more dense metals which may scatter encountered radiation.

Medical personnel in the medical facility 52 may be outfitted with the AR tracking device 46. The AR tracking device 46 may be configured to display a radiation scatter visualization 50 at the display portions 44 of the AR tracking devices 46 worn by each person. FIGS. 7 through 10 illustrate exemplary embodiments of the visualization 50 as it may appear to an individual wearing the AR tracking device 46. However, the visualization 50 may be displayed in the context of the user's position and/or gaze. Stated another way, FIGS. 7 through 10 illustrate what a user observes when wearing the AR tracking device 46 from a perspective view of the medical facility 52. The user may see the surgeon in the middle of the visualization 50 and others off to the sides of the visualization 50. The surgeon in the middle may see the visualization 50 all about them while looking at a patient on the operating table and/or seeing other equipment, such as but not limited to the equipment which scatters radiation 54, in the medical facility 52.

The visualization 50 may be generated and updated, at least in part, by a controller 56. The controller 56 may be configured to utilize one or more reference or registration points to virtually affix the visualization 50 relative to the personnel in the room such that the visualization 50 appears fixed as persons wearing the AR tracking devices 46 move about the room. The visualization 50, for example without limitation, may be virtually affixed relative to the radiation producing equipment 100, the radiation scattering equipment 54, other equipment, other part of the medical facility 52, the patient, some combination thereof, or the like.

In exemplary embodiments, without limitation, the controller 56 may be configured to process data stored in memory of a two or three-dimensional radiation intensity diagram 10, 20, underlying data regarding the same, or the like, for the particular equipment 100 being used in the room, along with other inputted or detected data such as the patient's body data, radiation scattering equipment 54 position data, equipment 100 position data, and/or type of other equipment, facility parameters, etc., as further explained below. The controller 56 may be located in the medical facility 52 or remote therefrom. The controller 56 may be in wired and/or wireless electronic communication with each AR tracking device 46, device 30, and/or tracking device 36 in the medical facility 52. The visualization 50 may be updated at the various AR tracking devices 46 by the controller 56 periodically or continuously. The visualization 50 may be updated in substantially real time, such as but not limited to, as data is received and processed accounting for normal delays due to transmission time, processing time, and the like.

The visualization 50 may comprise one or more shapes, text, lines, some combination thereof, or the like of the same or various types to represent the intensity of the radiation. In exemplary embodiments, the visualization 50 may comprise a multi-layered cloud or sphere, though any form of the visualization may be utilized. For example, without limitation, the visualization 50 may comprise a first color representing a high level of relative radiation intensity, a second color representing a medium level of relative radiation intensity, and a third color representing a low level of relative radiation intensity. The first color, for example without limitation, may comprise a shade of red, the second color a shade of orange, and the third color a shade of yellow. As another example, without limitation the first color may comprise a shade of red, the second color a shade of yellow, and the third color a shade of green. Any color, or combination of colors may be utilized.

As another example, the visualization 50 may comprise a multi-layered cloud or sphere where certain shapes are displayed at a first density to represent a low level of relative radiation intensity, a second density to represent a medium level of relative radiation intensity, and a third density to represent a high level of relative radiation intensity.

Any number of layers, colors, shapes, lines, text, some combination thereof, or the like may be utilized. Each change in layer, color, shape, line, text, some combination thereof, or the like may correspond with a change in level of relative radiation intensity. The visualization 50 may be displayed at a transparency sufficient to provide visibility of the patient and/or equipment through the visualization 50 yet of adequate opaqueness to call the visualization 50 to the user's attention. An exemplary transparency is at or below 20%, though any percentage may be utilized.

The various layers of the visualization 50 may be visible simultaneously such that the user can see each layer of the visualization 50. Alternatively, each layer of the visualization 50 may be visible only as the user approaches and/or enters the layer of the visualization 50.

As yet another example, without limitation, the visualization 50 may comprise one or more lights of monochromatic or multiple colors which becomes brighter or otherwise more intense as a user approaches the machine 100 or other area of higher relative radiation intensity. The one or more lights may be of monochromatic or multiple colors which becomes dimmer or otherwise less intense as a user steps away from the machine 100 or moves into areas of lower relative radiation intensity.

Alternatively, or additionally, one or more speakers 59 may be provided. The speakers 59 may be in electronic communication with the controller 56. The controller 56 may be configured to cause the speakers 59 to emit an audible tone(s) or message(s) regarding relative radiation intensity. For example, without limitation, the tones emitted may increase or otherwise differ in tone, frequency, pitch, amplitude, some combination thereof, or the like as the user approaches areas of relatively higher radiation intensity and decrease as the user approaches areas of relatively lower radiation intensity. Audible messages regarding the relative radiation intensity, or the like may be emitted.

Each AR tracking device 46 may be configured to provide a visualization 50 of the scattered radiation specific to the location and/or direction of gaze of the person wearing the AR tracking device 46. Personnel may move about the medical facility 52 and/or redirect their gaze and be provided with a substantially real-time update of the visualization 50 while still able to view the patient, the radiation producing equipment 100, the radiation scattering equipment 54, other equipment, and otherwise perform their duties. In this way, personnel may be appraised of at least the approximate level of relative radiation intensity in a given area in the room. Personnel may use the visualization 50 as a guide for adjusting their position within the medical facility 52, where possible, to minimize their exposure. For example, without limitation, a surgeon may lean backwards when activating the equipment 100 to minimize exposure. As another example, without limitation, an anesthesiologist who may not need to be physically close to the patient to perform his or her duties may position themselves outside of the visualization 50 to minimize his or her exposure. As yet another example, without limitation, a nurse may pull his or her hands away from the patient when the equipment 100 is active to move their hands from a relatively high to a relatively low area of relative radiation intensity.

The controller 56 may be configured to accept user input such as, but not limited to, at a touch screen interface, mouse, keyboard, voice recognition interface, some combination thereof, or the like. User input may include specification information for the machine 100, height of the patient, weight of the patient, radiation scatter, radiation intensity, radiation type, machine 100 settings, user preferences, some combination thereof, or the like. The controller 56 may comprise, or may receive, data regarding radiation intensity such as, but not limited to, data comprising or derived from the diagrams 10, 20 and/or other information provided from the manufacturer of the radiation producing medical equipment 100, radiation exposure measurement device 32, other sources, some combination thereof, or the like. The controller 56 may extract at least some of this information from the equipment 100. Alternatively, or additionally, at least some of this information may be provided by user input and/or via one or more memory ports, wired or wireless network communication, some combination thereof, or the like. The controller 56 may be configured to adjust the visualization 50 based on the input. Where no input is provided and/or found, default settings may be used. The default setting may be based on averages, conservative measures, margins of safety, industry standards, some combination thereof, or the like.

Figure 9:
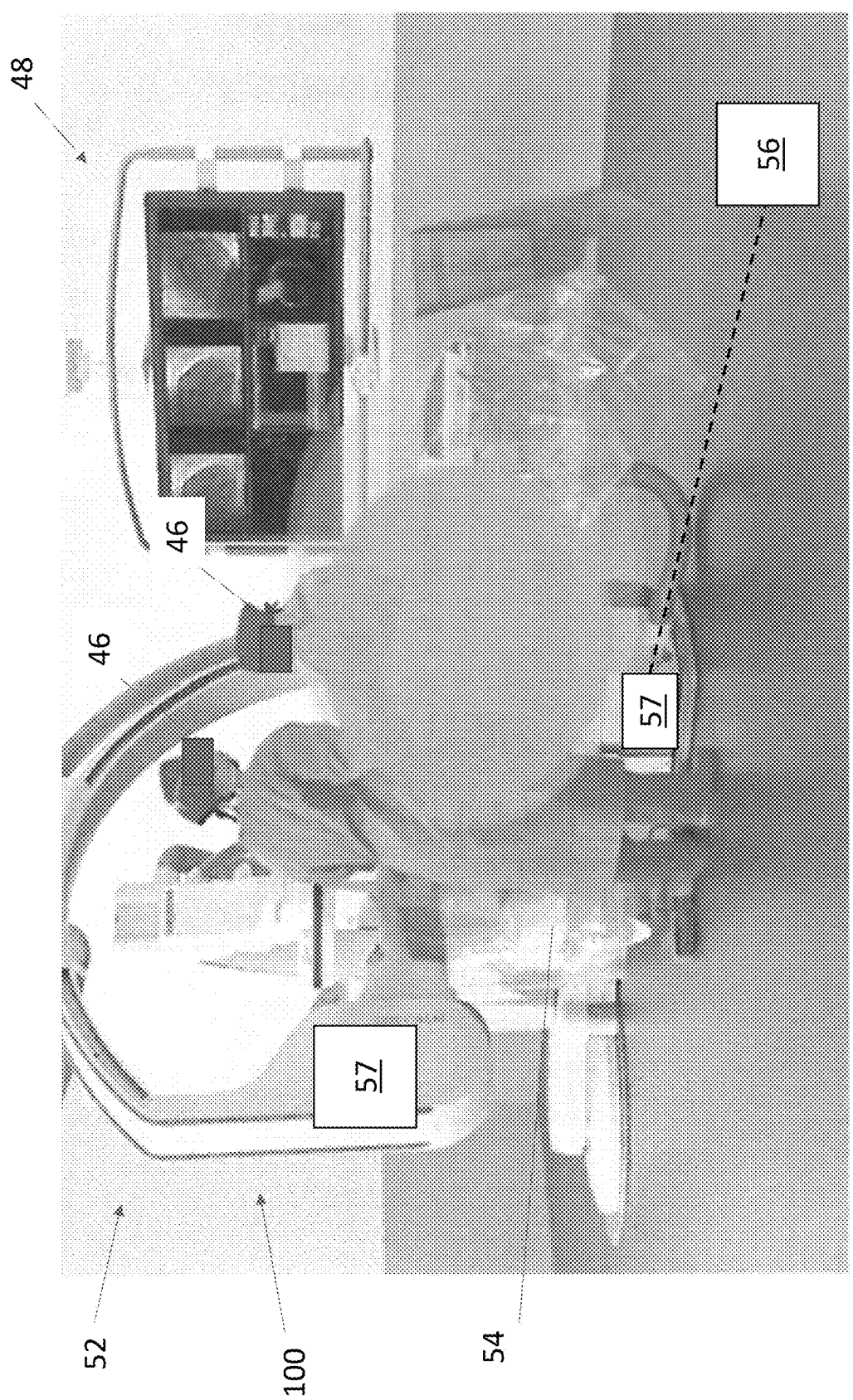
FIG. 9 is a perspective view of another exemplary medical facility with another exemplary radiation scatter visualization for the augmented reality system of FIG. 7.
Figure 10:
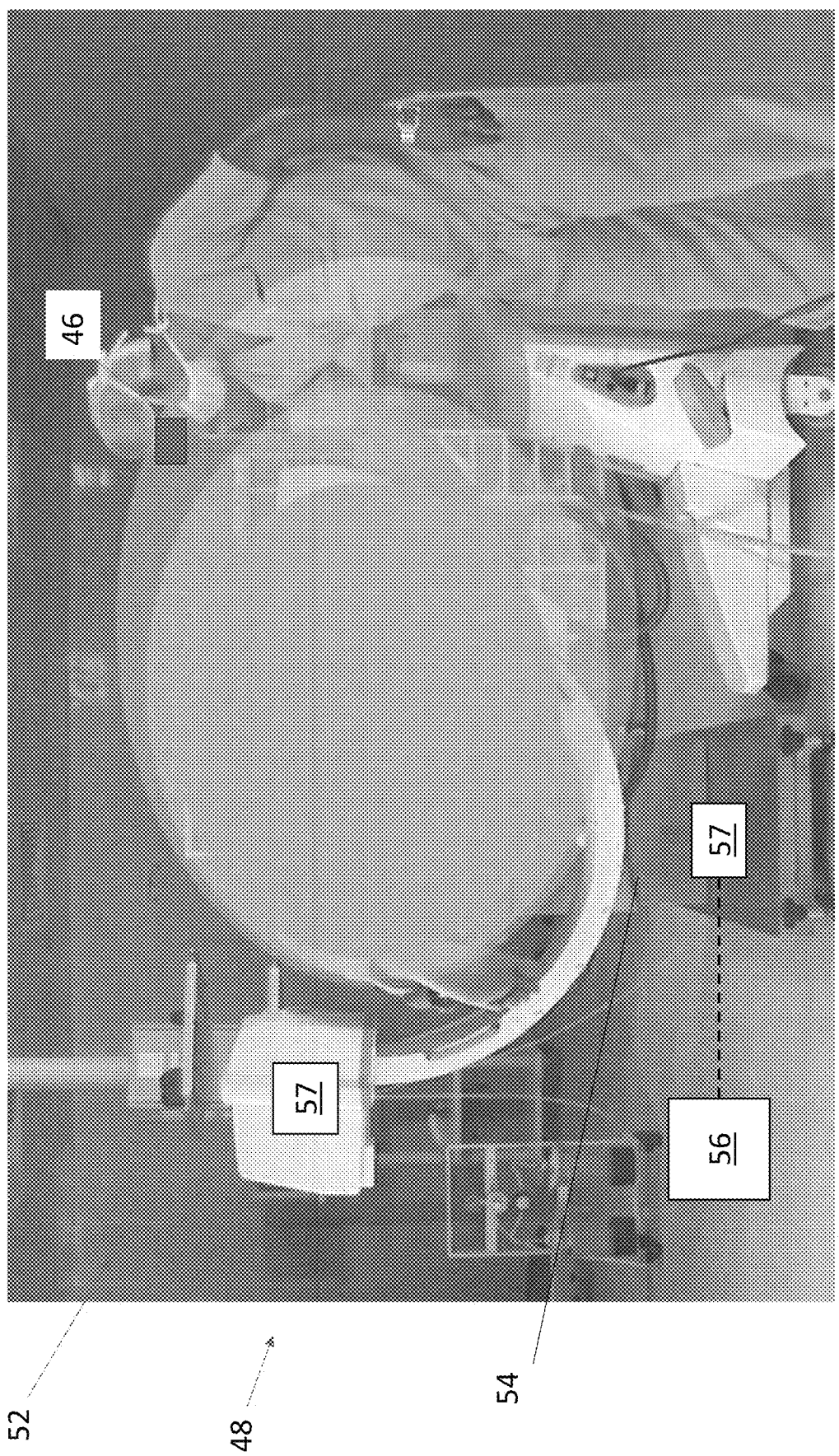
FIG. 10 is a perspective view of another exemplary medical facility with another exemplary radiation scatter visualization for the augmented reality system of FIG. 7.

The controller 56 may be configured to adjust the visualization 50 based on the position of the equipment 100. For example, without limitation, the equipment 100 may be raised, lowered, rotated, moved, swiveled, some combination thereof, or the like to perform various procedures. The equipment 100 may comprise one or more position tracking devices 57 configured to track the location and/or orientation of the equipment 100. The position tracking devices 57 may be in electronic communication with the controller 56. The controller 56 may be configured to adjust the visualization 50 based on the position of the radiation producing medical equipment 100. For example, FIG. 9 and FIG. 10 illustrates the machine 100 in a side orientation with the resulting visualization 50 skewed to the opposing side.

In exemplary embodiments, the equipment which scatters radiation 54 may comprise one or more position tracking devices 57 configured to track the location and/or orientation of the equipment which scatters radiation 54. The position tracking devices 57 may be in electronic communication with the controller 56. The controller 56 may be configured to adjust the visualization 50 based on the position of the equipment which scatters radiation 54. The same or similar equipment and techniques may be used for other items in the facility 52.

As another example, the radiation producing equipment 100 and/or the radiation scattering equipment 54 may be moved about the medical facility 52 to perform various tasks. The position of the visualization 50 may be moved with the radiation producing equipment 100 and/or the radiation scattering equipment 54.

In exemplary embodiments, the controller 56 may be configured to receive radiation exposure data from the radiation exposure measurement devices 32. The radiation exposure measurement devices 32 may be provided at the radiation tracking devices 30, the tracking devices 36, the AR tracking devices 46, some combination thereof, or the like. In exemplary embodiments, data from the radiation exposure measurement devices 32 may be used to validate and/or improve the visualization 50. The visualization 50 may provide qualitative type feedback while the radiation exposure measurement devices 32 may provide quantitative type feedback. Alternatively, or additionally, the radiation exposure data may be used to track personnel exposure levels. Radiation exposure data collected may be specific to certain parts of the body, in exemplary embodiments, and may be recoded as such.

In other exemplary embodiments, the medical facility 52 may comprise one or more training facilities and/or simulators. In such cases, the various equipment, such as but not limited to the radiation producing equipment 100, radioactive products, equipment which scatters radiation 54, other equipment, combinations thereof, or the like may be simulated or real. Other medical personnel and/or the patient may also, or alternatively, be simulated. The radiation emitted by the equipment 100 and scattered within the medical facility may be simulated and the visualization 50 may be provided to simulate such emitted and/or scattered radiation. This may be used to raise awareness of radiation exposure, train medical personnel, evaluate the impact of procedures on radiation exposure, test new procedures, combinations thereof, or the like.

Figure 11:
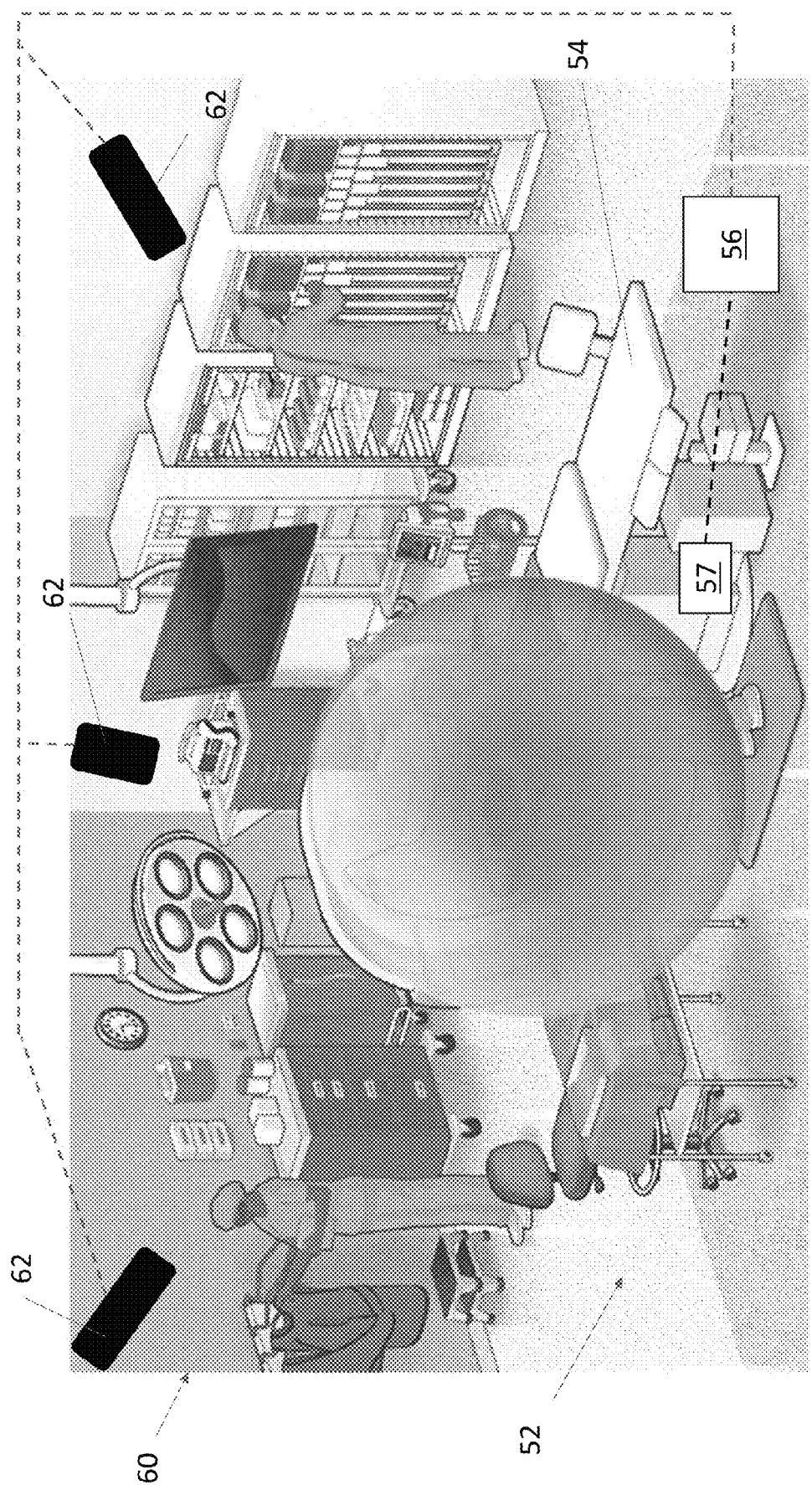
FIG. 11 is a perspective view of the medical facility and visualization of FIG. 7 with an exemplary projection system in accordance with the present invention.

FIG. 11 illustrates an exemplary projection system 60 for providing the visualization 50. One or more projection devices 62 may be provided in the medical facility 52. The projection devices 62 may be in electronic communication with the controller 56. The projection devices 62 may be configured to project the visualization 50 within the medical facility 52. The projection devices 60 may be configured to provide a three-dimensional or two-dimensional image which is viewable with or without other visual aid. For example, without limitation, the projection system 60 may utilize laser plasma technology, Pepper's Ghost effect, fan holograms, light field displays, lasers and mirrors, nologram technology, hologram technology, 3D volumetric technology, projection mapping technology, some combination thereof, or the like. The resulting visualization 50 may be provided in three-dimensions, or provided in two-dimensions with effects to make it appear three-dimensional to the viewer. The visualizations 50 of the radiation scatter in the room may be shown very accurately in one embodiment of the system of the present invention, or may be shown as informed approximations in another embodiment of the present invention, dependent upon how much data the user inputs into the system about the room, radiation scattering equipment 54, patient, radiation producing equipment 100, other equipment, other room parameters, and other factors affecting the scatter.

Figure 12:
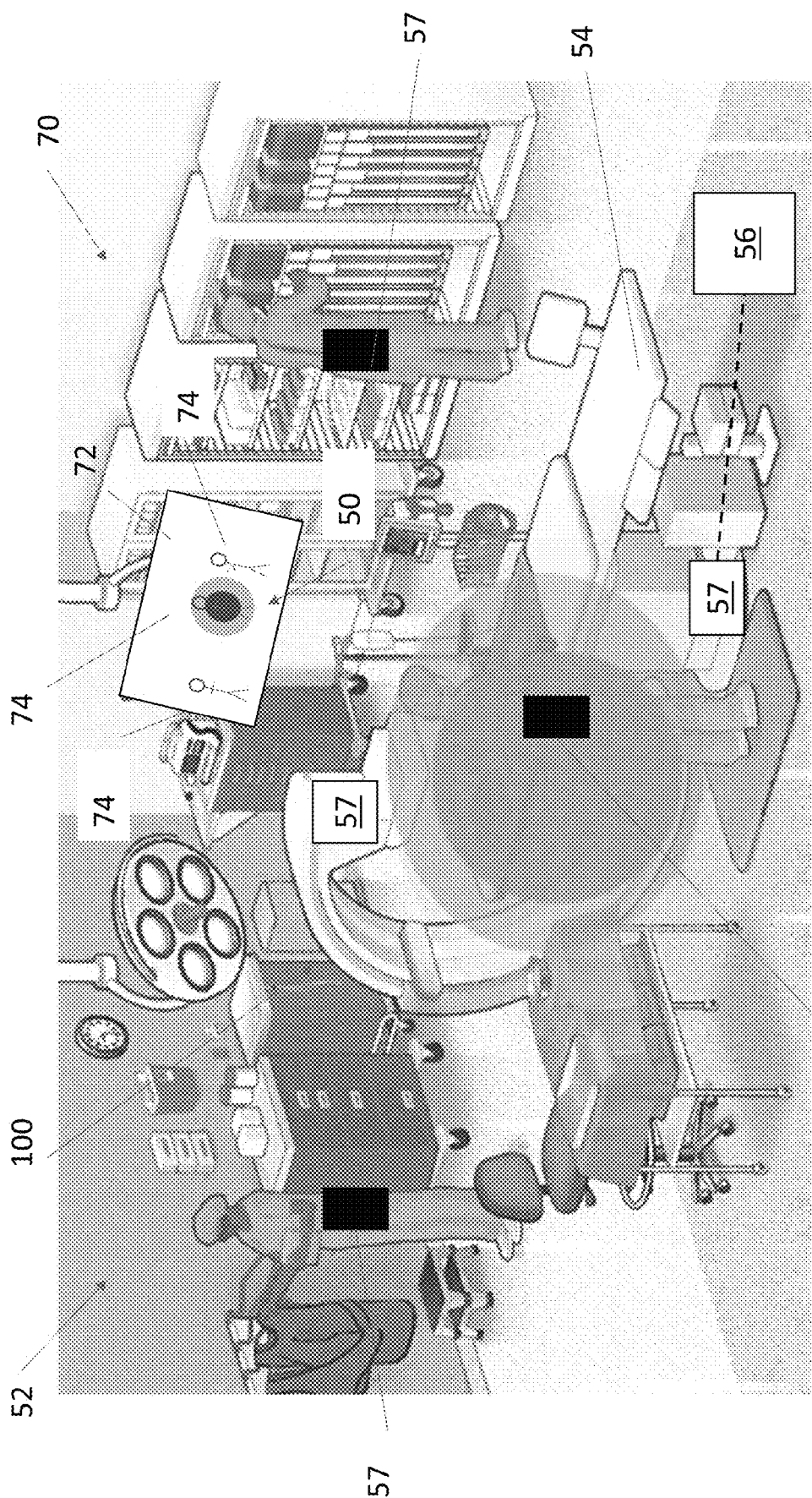
FIG. 12 is a perspective view of the medical facility and visualization of FIG. 7 with an exemplary electronic display system in accordance with the present invention.

FIG. 12 illustrates an exemplary electronic display system 70 for providing the visualization 50. One or more such electronic displays 72 may be located at the medical facility 52, though such is not required. Each electronic display 72 may be in electronic communication with the controller 56. The controller 56 may be configured to generate the visualization 50 at each electronic display 72. The controller 56 may be further configured to generate a representation of the medical personnel 74 in the medical facility 52 at the electronic display 72. In this way, the medical personnel may reference their representation 74 on the electronic display 72 relative to the visualization 50 to get an estimation of the radiation intensity where they are located. The representations 74 may comprise names, images, or other identifying information for the person.

The location of the personnel may be provided by way of position tracking devices 57 provided to each person. The position tracking devices 57 may be provided with the tracking devices 36, the AR tracking devices 46, as a standalone device, some combination thereof, or the like. The relative radiation intensity exposure, as determined by the personnel's distance from the equipment 100 for example, may be tracked based on position readings from the position tracking devices 57.

Figure 13:
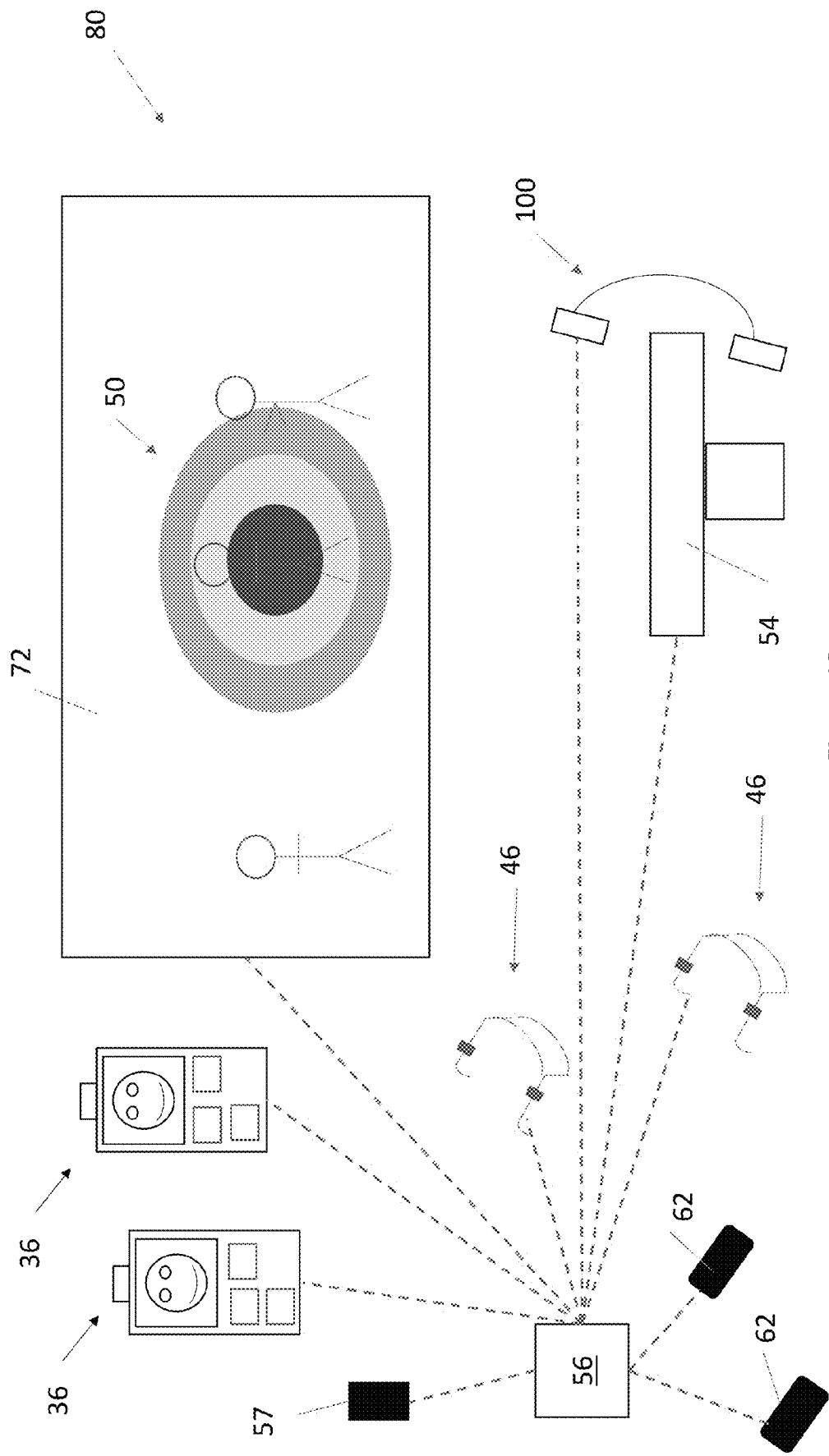
FIG. 13 is a simplified system diagram of an exemplary combined visualization system in accordance with the present invention.

FIG. 13 illustrates an exemplary combined system 80. The combined system 80 may utilize one or more of the tracking devices 36, the AR tracking devices 46, the electronic display 72, position tracking device 57, and the projection devices 62, in any combination and number. In this way, the combined system 50 may be provided at the AR tracking devices 46, the electronic display 72, and/or projected within the medical facility 52.

FIG. 14 illustrates a flow chart with exemplary logic for providing the visualization 50. User input regarding the patient height, the patient weight, and the type of machines 100 may be provided to the controller 56. The position of the radiation scattering medical equipment 54 may be determined. The position of the radiation producing medical equipment 100 may be determined. The position of the radiation producing equipment 100 and/or the radiation scattering equipment 54 may be determined by way of the respective position devices 57. The same, or different, such positioning devices 57 may be used on any number of items of equipment in the medical facility 52, such as but not limited to, the radiation producing medical equipment 100, the radiation scattering medical equipment 54, or other medical equipment. Examples of such equipment which may scatter radiation include, for example without limitation, operating tables, trays, medical devices, storage cabinets, shielding, metal surfaces, or the like. The controller 56 may be configured to adjust the visualization 50 to reflect the position and/or type of radiation producing medical equipment 100, radiations scattering equipment 54, or the like in the medical facility 52. Radiational absorbing equipment may also be similarly tracked, visualized, and/or factored in. Alternatively, or additionally, certain such equipment may be displayed or indicated to provide points of reference, realistic training scenarios, combinations thereof, or the like.

The position of the medical personnel may be determined. The position of the medical personnel may be determined by way of position tracking devices 57, the tracking devices 36, and/or the AR tracking devices 46. The visualization 50 may be generated. The visualization 50 may be provided at each of the AR tracking devices 46, the electronic displays 72, and/or the projection devices 62 within the medical facility 52. The visualization 50 may be updated as the position of the radiation producing equipment 100, the radiation scattering equipment 54, other equipment, and/or personnel changes. For example, equipment 54 which scatters, reflects, or otherwise alters the normal pathway of radiation may be desirable for tracking and factoring into the visualization 50, alternatively to or in addition to, equipment which produces radiation 100.

In exemplary embodiments, the controller 56 may be programmed with certain parameters of the medical facility 52, such as but not limited to, the size and/or shape of the physical space, including but not limited to, floor to ceiling height, wall locations, floor, ceiling, and/or wall materials, and the like as such parameters may affect radiation scatter. Such parameters may be used to adjust the visualization 50.

Figure 15B:
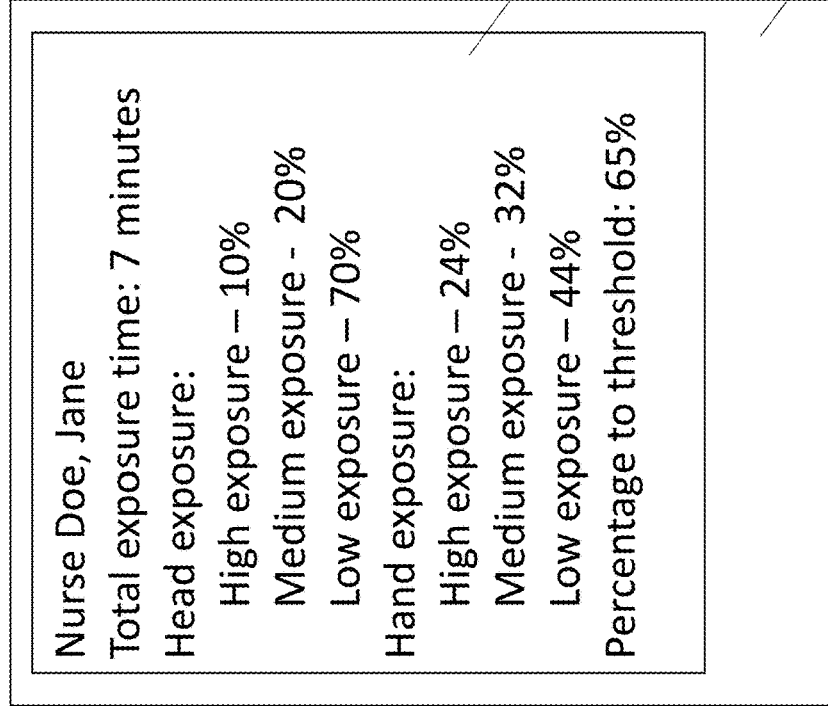
FIG. 15B is another exemplary exposure report.
Figure 15A:
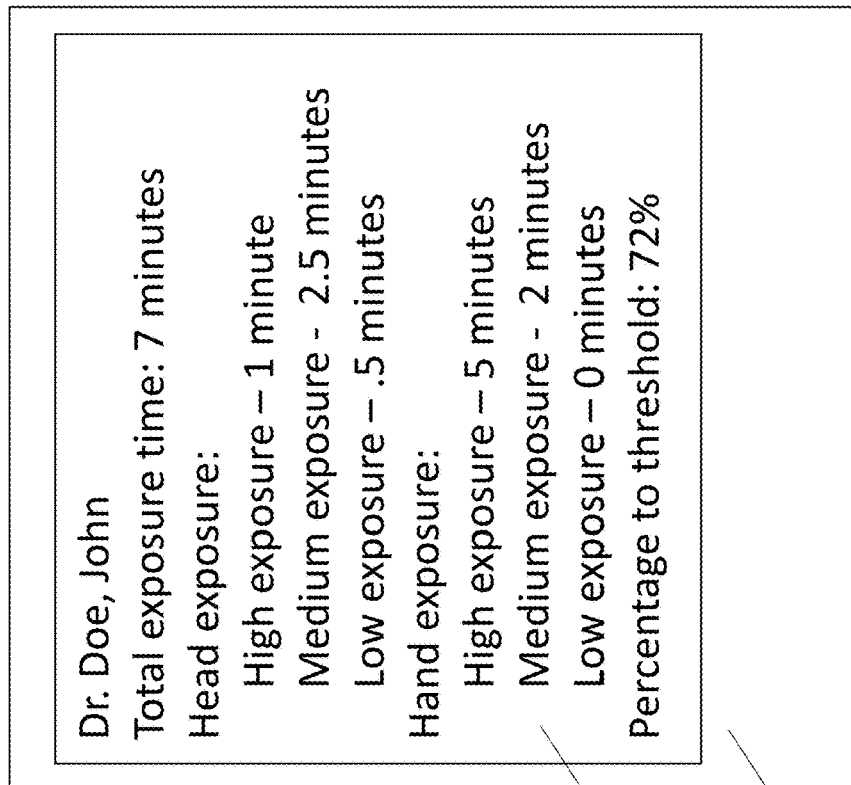
FIG. 15A is an exemplary exposure report in accordance with the present invention.

In exemplary embodiments, the visualization 50 may be provided only when the equipment 100 is active. Active may include, for example without limitation, one or more of being powered on, prepared for operation, emitting radiation, cooling down, some combination thereof, or the like. The visualization 50 may be provided for a margin of time before and/or after the equipment 100 is active. In other exemplary embodiments, the visualization 50 may be provided at all times. When the equipment 100 is active, or within the margin of time before and/or after being active, the visualization 50 may be changed. For example, without limitation, the visualization 50 may comprise a visible warning message, flashing, change of color, change of transparency, audible message, some combination thereof, or the like when the equipment 100 is active, or within the margin of time before and/or after being active. FIG. 15A and FIG. 15B illustrate exemplary exposure reports 200. Each exposure report 200 may comprise estimated relative exposure information for one or more persons. The exposure reports 200 may be generated, in whole or part, by the controller 56 in response to gathered data such as, but not limited to, exposure data and/or position data. Alternatively, or additionally, the exposure reports 200 may be generated, in whole or part, by data gathered directly from the various devices such as but not limited to, the AR tracking devices 46, the tracking devices 36, radiation exposure tracking devices 32, position tracking devices 57, some combination thereof, or the like. Alternatively, or additionally, the data from the controller 56 and/or the various devices may be transmitted to one or more remote databases for storage.

The exposure reports 200 may comprise identifying information for each individual such as but not limited to names, titles, photos, some combination thereof, or the like. The exposure reports 200 may comprise total estimated relative exposures information as well as estimated relative exposure information specific to certain parts of the body, such as but not limited to, head, arm, legs, torso, hands, feet, eyes, some combination thereof, or the like. Each category of estimated relative exposure (total and/or body part specific) may be broken down by areas of high, medium, and low relative radiation intensity exposure. Each category of exposure may be expressed as a time measurement, a percentage of total exposure time, some combination thereof, or the like.

The exposure reports 200 may comprise a percentage or other indication of progress towards a threshold, goal, or the like for a time period, such as the year, month, quarter, or the like.

Figure 16:
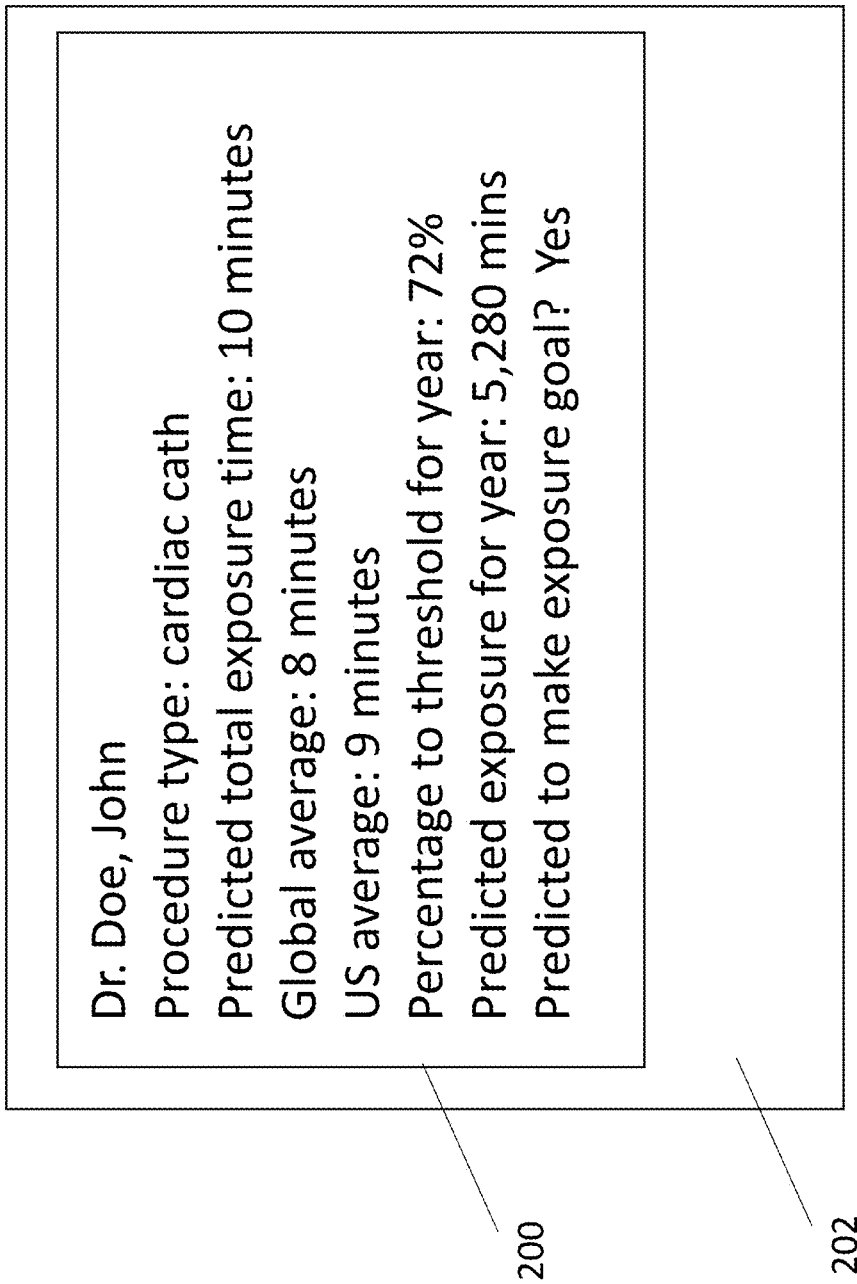
FIG. 16 is an exemplary predicted exposure report in accordance with the present invention.

FIG. 16 illustrates an exemplary predicted exposure report 300. Each predicted exposure report 300 may comprise estimated and/or predicted relative exposure information for one or more persons. The predicted exposure reports 300 may be generated by the controller 56 in response to gathered data such as, but not limited to, exposure data and/or position data. Alternatively, or additionally, the predicted exposure reports 300 may be generated, in whole or part, by data gathered directed from the various devices such as but not limited to, the AR tracking devices 46, the tracking devices 36, radiation exposure tracking devices 32, the position tracking devices 57, some combination thereof, or the like.

The predicted exposure reports 300 may comprise identifying information for the individual such as but not limited to name, title, photo, some combination thereof, or the like. The predicted exposure reports 300 may comprise procedure description information such as but not limited to name, CPT code, some combination thereof, or the like. The predicted exposure reports 300 may comprise a predicted total exposure time for the procedure. The predicted total exposure time may be based on average exposure during the same or similar procedures for the same person, facility averages, global averages, country specific averages, some combination thereof, or the like.

The predicted exposure reports 300 may comprise a percentage or other indication of progress towards a threshold for a time period, such as the year. The predicted exposure reports 300 may comprise predicted estimated total relative exposure for the time period, which may be expressed in a unit of time. The predicted exposure reports 300 may comprise a prediction of whether the reported individual will be under the threshold for the time period, such as but not limited to, a yes or no.

Information in the predicted exposure reports 300 may be determined by, entirely or in part, machine learning or other artificial intelligence software stored at the controller 56 or elsewhere. For example, without limitation, the individual's scheduled or predicted procedures for the year, as noted by CPT code or otherwise, may be retrieved and exposure time may be extrapolated based on personal averages, worldwide averages, country averages, facility averages, some combination thereof, or the like to determine total predicted exposure for the year. Each time a person using the disclosed systems or methods performs a procedure, the relative radiation intensity and/or related data may be stored at the controller 56 or elsewhere and associated with the procedure information, such as but not limited to by CPT code, such that said data may be utilized as part of the exposure reports 200, predicted exposure reports 300, machine learning or other artificial intelligence software, some combination thereof, or the like.

The exposure reports 200 and/or the predicted exposure reports 300, or data regarding the same, may be electronically communicated to one or more electronic devices 202 for display. The electronic devices 202 may comprise the electronic display 72, computers, tablets, smartphones, some combination thereof, or the like. The electronic devices 202 may be configured to generate all, or some, or the exposure reports 200 and/or predicted exposure reports 300.

The controller 56 and/or the electronic devices 202 may be configured to generate an alert when various exposure thresholds and/or predicted exposure thresholds are reached. Such thresholds may comprise yearly, monthly, or other time period limits, goals, or the like. For example, when 50% to the limit, 90% to the limit, and/or 100% to the limit is reached, an alert may be generated and transmitted. The recited thresholds are merely exemplary and are not intended to be limiting, any threshold or goal metric may be utilized. Such alerts may be transmitted as electronic notifications, audible messages (such as but not limited to from the speakers 59), displayed information at the AR tracking devices 46, displayed information at the electronic display 72, displayed information at the electronic devices 202, text messages, emails, automated calls, some combination thereof, or the like.

Several features and other aspects of the disclosures provided herein describe actions taken by the controller 56. However, it is contemplated that at least some of these actions may be determined, executed, or otherwise performed by controllers, processors, or other programmable logic devices located at the various devices such as but not limited to, the AR tracking devices 46, the projection devices 62, the tracking devices 36, the electronic display 80, other devices remote from the controller 56, some combination thereof, or the like.

It will be appreciated by those of skill in the art that the systems and/or methods shown and/or described herein may be used in conjunction with any type of healthcare setting, with any type of equipment, including but not necessarily limited to radiation producing and/or radiation scattering medical equipment, and/or to visualize any type of radiation potentially harmful to humans if exposed above what is generally considered to be safe levels or amounts, such as over many repeated exposures. Such types of radiation may be those defined by the Occupational Safety and Health Administration, Nuclear Regulatory Commission, Centers for Disease Control, the Food and Drug Administration, or other governmental or regulatory body, standards setting organization, combinations thereof, or the like.

Figure 17:
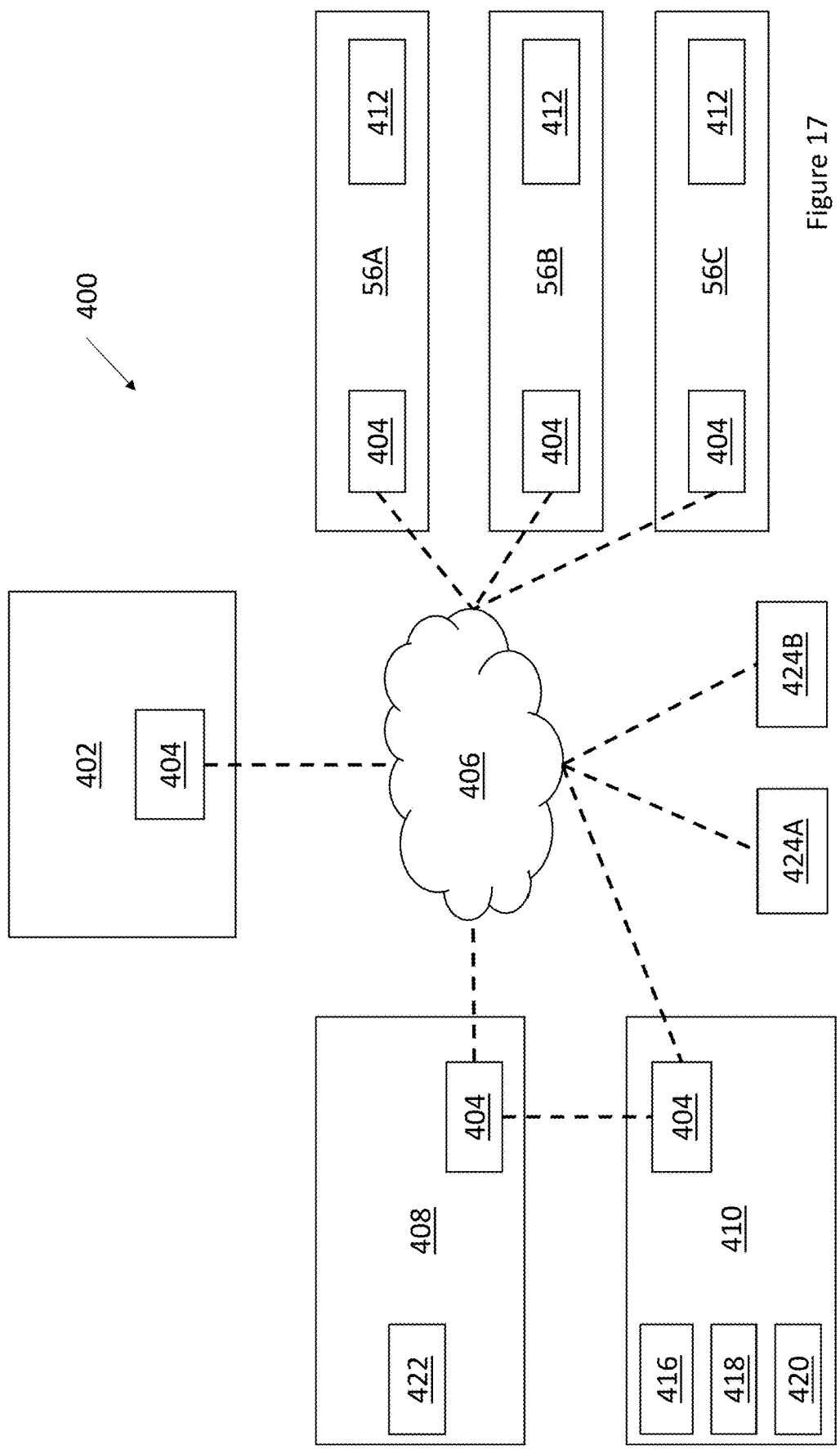
FIG. 17 is a plan view of an exemplary system for monitoring case progress by estimated radiation exposure for use with the systems and methods of FIGS. 1-16 in accordance with the present invention.

FIG. 17 illustrates a plan view of an exemplary system 400 for monitoring case progress and/or complexity by estimated radiation exposure. The system 400 may work in conjunction with some or all of the components shown and/or described with regard to FIGS. 1-16, though such is not required. For example, without limitation, the system 400 may work in conjunction with some or all of the components of the augmented reality system 48, the projection system 60, the electronic display system 70, the combined system 80, combinations thereof, or the like. In exemplary embodiments, without limitation, the system 400 may include the controller 56, or multiple such controllers 56A, 56B, 56C, such as in multiple operating rooms, medical facilities, and/or other facilities where radiation producing and/or scattering equipment is utilized. Any number of controllers 56 may be utilized.

The controllers 56 may be configured to gather and/or transmit data regarding radiation dosage, radiation scatter, personnel position, equipment position, patient and personnel demographic or other data, procedure information (e.g., CPT and/or IDC codes), equipment information (e.g., regarding radiation producing items and/or radiation scattering items), combinations thereof, or the like. The gathered information may be transmitted electronically to a database 402, or multiple such databases 402, for storage. The transmitted data may include, for example without limitation, the information shown and/or described with regard to FIGS.

15A-16, such as but not limited to, in the exposure reports 200, though any type of kind of information may be gathered, transmitted, and stored.

In exemplary embodiments, each controller 56 may comprise one or more timekeeping devices 412 configured to track date and/or time information in conjunction with received data, such as the radiation exposure data. In other exemplary embodiments, such timekeeping may be achieved at the individual components of the augmented reality system 48, the projection system 60, the electronic display system 70, and/or the combined system 80, such as but not limited to, the tracking device 36, the AR tracking device 46, the position tracking device 57, combinations thereof, or the like, or otherwise provided, and provided to the controllers 56. Such components may comprise timekeeping device 412 and the time and/or date information may be reported to the controllers 56 for recordation at the database(s) 402.

The database(s) 402 may be integrated with the controllers 56 or remote therefrom. Communication between the controllers 56 and the database 402 may be accomplished by way of network communication devices 404 at each respective device and one or more networks 406.

An analytics subsystem 408 may be configured to process some or all of the data stored at the database 402. The analytics subsystem 408 may be integrated with the controllers 56 and/or database 402, or may be remote therefrom and in electronic communication with the same by way of said network communication devices 404 and networks 406. The analytics subsystem 408 may comprise one or more executable software routines configured to analyze the stored estimated radiation exposure data and other information to generate various benchmarks, reports, and/or measures, which may be used to trigger interventions as further discussed herein. Such software routines may comprise, for example without limitation, one or more machine learning algorithms, artificial intelligence algorithms, combinations thereof, or the like. For example, without limitation, the analytics subsystem 408 may be configured to utilize supervised learning, unsupervised learning, and/or semi-supervised learning techniques, regression, instance-based, regularization, decision tree, Bayesian, clustering, associated rule learning, artificial neural network, deep learning, dimensional reduction, and/or ensemble algorithms or analysis, combinations thereof, or the like, to name a few examples. Any known or yet to be developed algorithms, analysis, and/or techniques may be utilized. Such analysis and development of benchmarks may be performed automatically and/or on-demand. The benchmarks may be updated periodically, such as upon receipt of additional data at the database 402 from the controller(s) 56.

An intervention subsystem 410 may be configured to provide various interventions based on findings made by the analytics subsystem 408 as further discussed herein. The intervention subsystem 410 may be integrated with the controllers 56, database 402, and/or analytics subsystem 408, or may be remote therefrom and in electronic communication with the same by way of said network communication devices 404 and networks 406. For example, without limitation, where the analytics subsystem 408 finds that one or more benchmarks for a given procedure are met or exceeded by a predetermined amount, the intervention subsystem 410 may be configured to provide one or more interventions. The type, kind, or number of interventions provided may be specific to the procedure performed, the recipient of the intervention, the benchmarks met or exceeded, user preference, personnel information, medical facility information, procedure status (e.g., underway or post-operative), combinations thereof, or the like.

The controllers 56, database 402, and analytics subsystem 408 may comprise any type or kind of electronic device such as, but not limited to, computers, electronic storage devices, processors, servers, combinations thereof, or the like. Such electronic devices may be the same or different across the controller 56, database 402, and/or analytics subsystem 408.

The analytics subsystem 408 may comprise a predictive module 422. The predictive module 422 may be configured to generate predicted exposure levels for the personnel. The predictive module 422 may be configured to utilize extrapolation, artificial intelligence, and/or machine learning techniques or algorithms to determine predicted exposure levels for personnel over a period of time (e.g., day, week, year, career, etc.). For example, without limitation, an operator's predicted exposure for a period of time may be generated based on a number and type of prior procedures performed, operator certification, training, experience level, combinations thereof, or the like. The database 402 may be queried to retrieve data relevant to such specifics and an average or other measure of exposure per procedure may be generated. The operator's predicted number of procedures, of the same or different type, for the time period may be developed based on the operator's history or averages for similarly situated operators, and the average or other value may be multiplied by the predicted number of procedures to develop a predicted exposure value. The predicted value may be added to any current cumulative values to predict a cumulated exposure level for a future time period. The prediction may also be based on scheduled cases. The same or similar techniques may be utilized for other personnel including nurses, assistants, anesthesiologists, combinations thereof, or the like. These examples are provided to be illustrative and are made without limitation.

FIG. 18 illustrates an exemplary profile 414 which may be generated by the analytics subsystem 408. The profiles 414 may be generated on-demand or periodically. The analytics subsystem 408 may be configured to send data sufficient to generate the profile 414 at any number of remotely connected electronic devices, including but not limited to, the AR tracking devices 46, by way of the projection devices 62, at the electronic displays 72, at one or more remote electronic devices 424A, 424B (e.g., computer, server, tablet, smartphone, etc.), combinations thereof, or the like. Any number or type of remote electronic devices 424 may be utilized. For example, without limitation, the remote electronic devices 424 may be associated with hospital or medical practice administrators, personnel, insurance providers, medical device companies, combinations thereof, or the like.

The profile 414 may comprise any type of kind of data tracked by the system 400. For example, without limitation, the profile 414 may comprise a photo or other visual depiction of the individual with which the profile is associated (e.g., the operator or other personnel), name and other demographic information for the individual, practice area, certifications and/or completed trainings, associated hospital or other practice information, experience information, age, average or other measure of estimated radiation exposure per procedure, average or other measure of actual radiation exposure (e.g., as measured by the radiation exposure measurement devices 32), cumulative estimated and/or actual radiation exposure information for a given time period (e.g., year, month, quarter, etc.), procedure information (e.g., CPT, IDC, or other code, date and time information, exposure information, radiation producing equipment used, radiation scattering items used, medical devices used, procedure techniques used, patient information, etc.), average or other measure of number of procedures for a given time period (e.g., year, month, quarter, etc.), combinations thereof, or the like.

The profiles 414 may, alternatively or additionally, be developed for hospitals, medical practices, medical facilities, medical groups, geographic regions, procedures, combinations thereof, or the like. The profiles 414, or underlying data, may be utilized by personnel, hospital or practice administrators, peers, medical societies, medical device representative or companies, combinations thereof, or the like to target candidates for further training and/or education, management and workload balancing, marketing opportunity, development or commercialization opportunities, combinations thereof, or the like. The profiles 414 and related data may be depersonalized or otherwise deidentified in exemplary embodiments, though such is not required. To name a few examples, without limitation, hospitals may identify operators whose procedures typically result in higher exposure levels and target those candidates for further training or education. Medical device companies may identify procedures, or parts or procedures, having higher exposure levels and develop new devices or techniques for those procedures. Hospitals, medical device companies, or insurance companies may identify practices with higher exposure levels for particular procedures and suggest investment in newer equipment or training of new techniques.

A profile 414 may be generated for each personnel associated with one or more tracking devices 36 and/or AR tracking devices 46 or otherwise registered with the system 400. However, such profiles 414 may, alternatively or additionally, be generated for certain such personnel, such as on an on-demand basis for a subset of such personnel. For example, without limitation, a hospital administrator may generate a profile for all personnel associated with a particular practice group. As another example, a profile 414 may be generated for each personnel at approximately each anniversary of hiring as part of an annual review process.

The database 402 may form part of, or be in electronic communication with, an electronic health record ("EHR") system. Alternatively, or additionally, the controllers 56 may be in electronic communication with said EHR system. In this way, radiation exposure (actual and/or estimated) and other procedure information for said patient and/or said personnel may be stored at said EHR system. One or more of the remote devices 424 may comprise one or more EHR systems, in exemplary embodiments.

Figure 19:
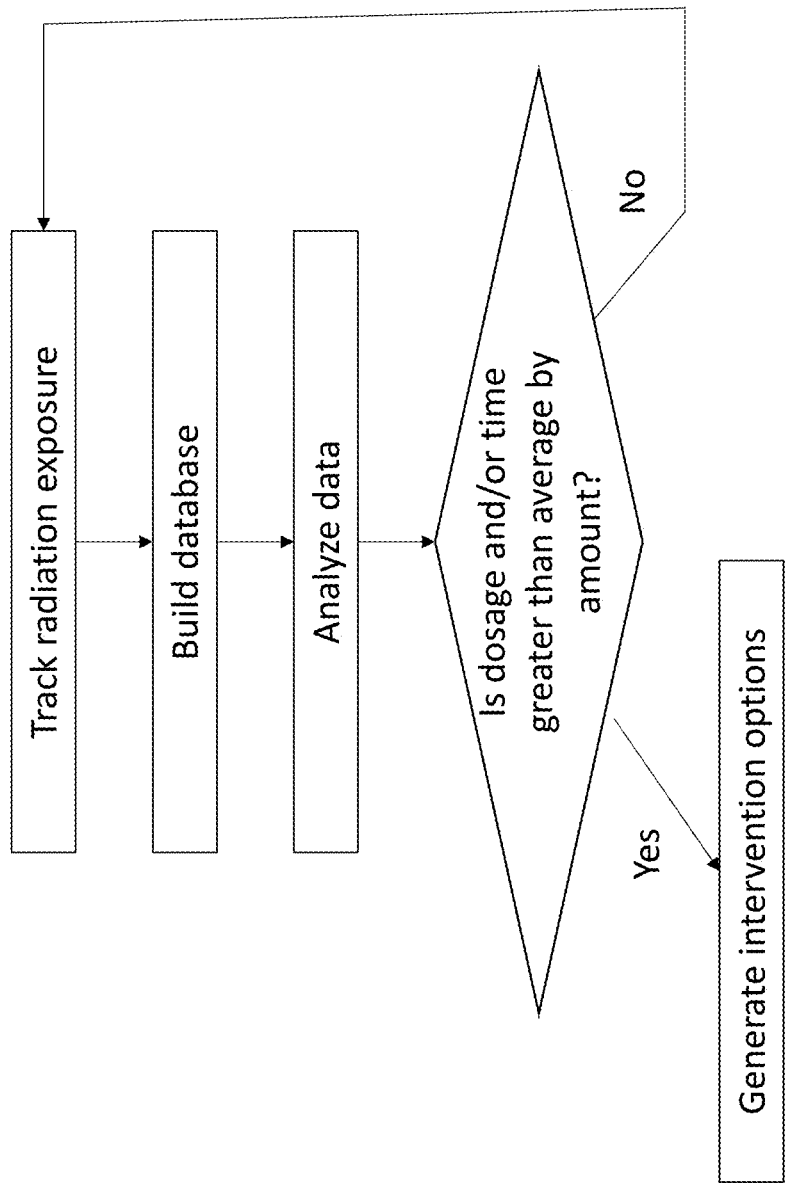
FIG. 19 is a flow chart with exemplary logic for operating the system of FIG. 17.

FIG. 19 illustrates exemplary logic for use with the system 400. The radiation exposure data (actual and/or estimated) may be tracked, such as by way of the augmented reality system 48, the projection system 60, the electronic display system 70, and/or combined system 80, the tracking device 36, the AR tracking device 46, the position tracking device 57, combinations thereof, or the like. Such data may be tracked over multiple procedures associated with multiple personnel, patients, and/or medical facilities. This data may be used to build a data set within the database 402. The data may be analyzed by way of the analytics subsystem 408.

In exemplary embodiments, estimated and/or actual exposure levels may be cumulated for a given procedure for purposes of triggering interventions. The analytics subsystem 408 may determine radiation exposure for each instance radiation producing medical equipment 100 is activated, such as but not limited to, the position of each personnel as determined by the tracking device 36, the AR tracking device 46, the position tracking device 57 relative to the radiation scatter intensity field data 10 associated with the radiation producing medical equipment 100 activated. Such exposure may be compared against the benchmarks by the analytics subsystem 408 for each instance of exposure. Alternatively, or additionally, such exposure may be cumulated for a given procedure against the benchmarks by the analytics subsystem 408. Such individual or cumulative exposures against benchmarks may be used to trigger interventions from the intervention subsystem 410.

The analytics subsystem 408 may be configured to generate various benchmarks based on the data set at the database 402. For example, without limitation, the analytics subsystem 408 may generate average radiation exposure data for various procedures, such as but not limited to, as classified by CPT code, IDC code, or other classification, technique(s) used, equipment used, combinations thereof, or the like. As another example, the average radiation exposure data may be analyzed by hospital, practice, operator information (e.g., age, experience, training, associated hospital or practice, etc.), medical staff information, geographic region, patient information (e.g., demographics, presenting symptoms, outcome, etc.), experience, training, certification, procedures using similar equipment or techniques, equipment used (e.g., radiation producing equipment, radiation scattering equipment, medical devices utilized) combinations thereof, or the like. Essentially, radiation exposure may be measured as a surrogate for case complexity and/or progress. In exemplary embodiment, the radiation exposure may be estimated exposure levels based on personnel position within estimated radiation scatter, but actual radiation exposure measurements may alternatively or additionally be used. The benchmarks may include any type or kind of measure including, but not limited, averages, medians, modes, maximums, minimums, ranges, predictions, combinations thereof, or the like.

The analytics subsystem 408 and/or the intervention subsystem 410 may be configured to determine where one or more particular procedures has met, not met, exceeded, or fallen short of one or more benchmarks, such as by a predetermined amount, and the intervention subsystem 410 may be configured to initiate one or more appropriate interventions. These benchmarks may be average, median, modes, maximum, minimum, or other measure of estimated or actual exposure levels for similar cases. Similar cases may be where, for example without limitation, the same or similar procedures are performed, the same or similarly situated operators performs the same or similar procedures, the procedures are performed at the same hospital or practice, within a given geographic area, and/or on similarly situated patients, where the same or similar techniques and/or devices are used, combinations thereof, or the like. Similarly situated operators may be those having the same level of experience, certification, training, combination thereof, or the like.

Where a benchmark is met, not met, exceeded by a predetermined threshold, combinations thereof, or the like, one or more interventions may be initiated. The analysis and/or interventions may be initiated during a procedure, during post-operative review, or periodically, such as during quarterly, annual, etc. reviews. For example, without limitation, the interventions may include providing the operator or other personnel with access to medical literature, training videos or information, educational opportunities, auditory or visual feedback, audio and/or visual communication with another operator or medical staff, combinations thereof, or the like. Such access may be facilitated by way of one or more reference databases 416 integrated with, or remote from and in electronic communication with, the intervention subsystem 410. In exemplary embodiments, during a procedure if a benchmark exposure level is met, not met, exceeded, or fallen short of, this may indicate that the procedure is more complex than anticipated and/or that the procedure is not progressing as expected. An audible or visible indicator of the same may be generated by a notification subsystem 418, such as at the AR tracking devices 46, the projection devices 62, the electronic display 72, the remote devices 424, a speaker, combinations thereof, or the like. The audible or visible indicator may alert the personnel to the unanticipated complexity and/or progress (or lack thereof). Options to access training or educational materials, such as those stored at the reference databases 416, may be provided, such as at the AR tracking devices 46, the projection devices 62, the electronic display 72, and/or the remote devices 424, to facilitate further case progress, either in substantially real-time or post-operative such as for further training and education. Such training materials may provide latest or alternative techniques, equipment available for use in such procedures, combinations thereof, or the like. Alternatively, or additionally, virtual consults with other operators, medical staff, technical support representatives (particularly in the case of operating certain medical devices) may be provided such as at the AR tracking devices 46, the projection devices 62, the electronic display 72, and/or the remote devices 424, by way of one or more communication subsystem 420. The communication subsystems 420 may be integrated with, or remote from, the intervention subsystem 410. The communication subsystems 420 may be configured to facilitate videoconferencing, telephonic conferencing, or other visual and/or audio-based communication between personnel in the medical facility performing the procedure and remote personnel. Alternatively, or additionally, the communication subsystems 420 may be configured to provide electronic access to a chatbot, artificial intelligence machine, combinations thereof, or the like.

To give an example, without limitation, where an estimated exposure level for a procedure underway, as determined by at the analytics subsystem 408 from information obtained by way of the controller 56, exceeds a benchmark developed by the analytics subsystem 408 based on data stored at the database 402 by at least a predetermined amount, the intervention subsystem 410 may be configured to transmit a notification, such as generated by the notification subsystem 418, to the tracking device 36 and/or AR tracking device 46 associated with the personnel for whom the estimated exposure level has exceeded the benchmark. The notification may include, for example, an invitation to review educational or training literature stored at the reference databases 416, conference in a more experienced operator by way of the communications subsystem 420, combinations thereof, or the like. Acceptance of the invitation may be configured to cause such literature or conference to proceed at the display portion 44 of the AR tracking device 46, for example without limitation.

To give another example, without limitation, where an operator consistently has higher than average exposure for a procedure, the intervention subsystem 410 may be configured to provide a notification, such as by way of the notification subsystem 418, to the controller 56 and/or remote devices 424 to the operator, medical staff, hospital administrators, etc. post procedure completion noting the higher-than-average exposure and suggest further training and/or education, such as by way of the reference databases 416, the use of new or different medical devices to shorten procedure time and/or reduce radiation exposure, or provide the operator with a post-operative consult with a more experienced operator. The consult may alternatively take place through the remote devices 424, though such is not required.

The intervention subsystem 410 may be configured to provide interventions specific to the personnel, the procedure, equipment or technique used, user preference, the medical facility, the status of the procedure, the benchmark (s), the amount the benchmark(s) is exceeded or fallen short of, combinations thereof, or the like.

Such interventions may be generated in response to perceived case complexity or lack of progress as measured by estimated or actual radiation. However, such interventions may, alternatively or additionally, be provided proactively, such as to facilitate various radiation safety measures or preemptive training or education programs.

While entire procedures are discussed in at least some instances, the systems and methods shown and/or described herein may be utilized to analyze particular segments, sub-procedures, or parts of a given procedure. For example, without limitation, where the benchmark(s) are exceeded for particular portions of particular procedures, or sub-procedures within a larger procedure, those portion(s) may be identified as being particularly complex or problematic. Interventions specific to those portions of procedures may be provided.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers or specialized computing devices. The electronic devices may comprise personal computers, smartphone, tablets, databases, servers, or the like. The electronic connections and transmissions described herein may be accomplished by wired or wireless means. The computerized hardware, software, components, systems, steps, methods, and/or processes described herein may serve to improve the speed of the computerized hardware, software, systems, steps, methods, and/or processes described herein.

What is claimed is:

1. A system for monitoring progress of a medical procedure by radiation exposure, said system comprising:
    a tracking device associated with an individual assisting with performance of the medical procedure and comprising:
        a position tracking device; and
        a body attachment portion configured to facilitate securement of said tracking device to a portion of a body of the individual;

an intervention subsystem;
an analytics subsystem; and
a controller in electronic communication with the tracking device, the analytics subsystem, and the intervention subsystem, wherein said controller comprises executable software instructions stored at one or more electronic storage devices, which when executed, configure one or more processors to:
receive a first location for a first medical equipment item used for the medical procedure, wherein the first medical equipment item is configured to produce radiation for medical treatment purposes ("radiation device");
receive a second location for a second medical equipment item used for the medical procedure, wherein the second medical equipment item is known to scatter radiation produced by the radiation device ("radiation scattering item");
receive position data from the tracking device continuously or periodically throughout the medical procedure, wherein each measurement provided by said position data is associated with a time;
receive data indicating one or more instances radiation is produced by said radiation device and scattered by said radiation scattering item, wherein said data indicates at time, approximate distance of scatter, and approximate intensity of radiation on a distance specific basis to define a radiation scatter intensity field at each of said one or more instances;
determine, by way of said analytical subsystem, an estimated exposure level for the individual based on the position of the individual relative to the radiation scatter intensity field at each of the instances the radiation device is activated;
compare the estimated exposure level of the individual to a benchmark; and
if the estimated exposure level for the individual exceeds the benchmark by at least a predetermined amount, provide, by way of the intervention subsystem, an intervention at the tracking device.

2. The system of claim 1 wherein:
said controller is configured to, by way of said analytical subsystem, cumulate said estimated exposure levels for the individual for each of the instances the radiation device is activated for comparison against the benchmark.

3. The system of claim 1 wherein:
the tracking device is configured to provide an augmented reality ("AR") experience at a lens.

4. The system of claim 3 wherein:
said controller is configured to generate a visualization at the lens of the scattered radiation in a fashion reflecting a last one of the measurements from the position data for the tracking devices at the time of display;
said controller is configured to update said visualization as new position data is received for the tracking devices.

5. The system of claim 4 further comprising:
a first position sensor provided at the radiation device, wherein said radiation device is position adjustable relative to said radiation scattering item;
a second position sensor provided at the radiation scattering item, wherein said radiation scattering item is position adjustable relative to said radiation device; and additional software instructions at the one or more electronic storage devices of said controller, which when executed, configure said one or more processors of said controller to:
receive position data from said first position sensor associated with said radiation device;
use said received position data for said radiation device to determine said first location;
receive position data from said second position sensor associated with said radiation scattering item;
use said received position data for said radiation scattering item to determine said second location;
receive new position data from said first position sensor associated with said radiation device or said second position sensor associated with said radiation scattering item; and
adjust said visualization at the lens to visually reflect an updated radiation scatter intensity field due to a new position of said radiation device relative to said radiation scattering item.

6. The system of claim 5 wherein:
said medical facility comprises an operating room;
said radiation device comprises an imaging device; and
said radiation scattering item comprises an operating table.

7. The system of claim 3 wherein:
said intervention subsystem is configured to electronically display, at said lens of at least one of said AR tracking devices, medical literature or training materials for at least part of said intervention.

8. The system of claim 3 wherein:
said intervention subsystem comprises a communications subsystem configured to electronically facilitate, at said lens of at least one of said AR tracking devices as well as through an associated microphone and speaker, videoconferencing for at least part of said intervention.

9. The system of claim 1 wherein:
said controller is configured to:
receive data indicating a type of the radiation device;
receive data indicating a type of the radiation scattering item; and
retrieve radiation scatter intensity field information specific to said type of radiation device, said type of radiation scattering item, and said first location relative to said second location to determine said radiation scatter.

10. The system of claim 1 further comprising:
a number of additional ones of said tracking device in electronic communication with said controller;
a number of additional ones of said controller, each in electronic communication with additional ones of said tracking device and associated with a different medical facility; and
a database in electronic communication with said controller and said number of additional ones of said controller, wherein said database is configured to store estimated exposure levels for a number of medical procedures as received by said controller and said number of additional ones of said controller build a data set of said estimated exposure levels, wherein each of said estimated exposure levels is associated with one of a number of medical procedure codes, and wherein said analytics subsystem comprises one or more algorithms configured to generate, from said data set, said benchmarks.

11. The system of claim 10 wherein:
said benchmarks comprise average exposure levels for one or more medical procedures associated with a given one of said medical procedure codes.

12. The system of claim 10 wherein:
said benchmarks are specific to an associated one of the medical facilities where said medical procedure is performed.

13. The system of claim 10 wherein:
said analytics subsystem is configured to generate, for display at one or more remote electronic devices, a personnel profile for a respective one of said individuals associated with any one of said tracking device and said additional ones of said tracking device.

14. The system of claim 13 wherein:
said personnel profile comprises demographic, training or certification, associated medical practice, experience, and exposure information for a respective one of said individuals.

15. The system of claim 10 wherein:
said database is configured to store date and time information in association with each of said estimated exposure levels.

16. A method for monitoring progress of a medical procedure by radiation exposure, said method comprising the steps of:
receiving, at a controller, a first location for a first medical equipment item used for the medical procedure and configured to produce radiation for medical treatment purposes ("radiation device");
receiving, at the controller, a second location for a second medical equipment item used for the medical procedure which is known to scatter radiation produced by the radiation device ("radiation scattering item");
tracking, by way of a number of tracking devices, positions of a number of individuals assisting with performance of the medical procedure;
receiving, at the controller, the positions of the individuals as tracked by the tracking devices at intervals during the medical procedure, wherein each of the positions is associated with a time;
receiving, at the controller, data indicating one or more instances radiation is produced by said radiation device and scattered by said radiation scattering item, wherein said data indicates a time, approximate distance of scatter, and approximate intensity of radiation on a distance specific basis to define a radiation scatter intensity field at each of said one or more instances;
determining, by way of an analytics subsystem associated with said controller, an estimated cumulative exposure level for each of the individuals during said medical procedure based on the positions of each individual within the radiation scatter intensity field at each of the instances the radiation device is activated; and
comparing, by way of the analytics subsystem, the estimated cumulative exposure level of each of the individuals to one or more benchmarks.

17. The method of claim 16 further comprising the steps of: determining, by way of the analytics subsystem, that the estimated cumulative exposure level for at least one of the individuals exceeds at least one of the benchmarks by at least a predetermined amount.

18. The method of claim 17 further comprising the steps of:
receiving, from said controller and a number of additional ones of said controllers, each in electronic communication with a number of additional ones of said tracking device, each associated with an individual, estimated cumulative exposure levels for a number of additional medical procedures;
building a data set of said estimated cumulative exposure levels at a database, wherein each of said estimated cumulative exposure levels is associated with one of said individuals and one of a number of medical procedure codes; and
applying, by way of said analytics subsystem, one or more machine learning or artificial intelligence-based algorithms to said data set to develop said benchmarks.

19. The method of claim 17 further comprising the steps of: generating, by way of an intervention subsystem, an intervention at each respective one of the tracking devices associated with each of the at least one of the individuals.

20. The method of claim 19 wherein:
each of said tracking devices comprise an augmented reality device configured to, by way of said controller, generate an overlay visualization of said scattered radiation at a display portion of said tracking device during said medical procedure; and
said controller is configured to update said visualization as new position data is received for said tracking devices, said radiation device, and said radiation scattering item.

21. The method of claim 20 wherein: the step of generating said intervention comprises prompting said individual to initiate a videoconference, utilizing said tracking device, with another one of said individuals having more experience than said individual while said medical procedure is underway and providing said videoconference at said tracking device or electronically displaying, at said display portion of said tracking device, educational or training reference materials for said medical procedure.

22. A system for monitoring progress of medical procedures by radiation exposure, said system comprising:
a number of augmented reality ("AR") tracking devices, each associated with one of a number of individuals which assist with performance of medical procedures at medical facilities, each respective one of said AR tracking devices comprising:
a display portion comprising a transparent or translucent material and configured to display one or more images for a respective one of the individuals to view as an overlay to a respective one of said medical facilities while a respective one the medical procedures is underway;
a position tracking device configured to track a position of the respective one of the individuals while the respective one of the medical procedures is underway; and
a body attachment portion configured to facilitate securement of said AR tracking device to a portion of a body of the respective one of the individuals such that the display portion is normally visible to the respective one of the individuals;
a number of controllers, each in electronic communication with a subset of the number of AR tracking devices;
a database in electronic communication with each of said number of controllers;
one or more intervention subsystems, each in electronic communication with one or more of the number of controllers and comprising a notification subsystem;
one or more reference databases in electronic communication with said one or more intervention subsystems;

one or more analytics subsystems, each in electronic communication with one or more of the number of controllers; and executable software instructions stored at one or more electronic storage devices associated with the number of controllers, which when executed, configure one or more processors to:

receive location data for medical equipment items used for the medical procedures configured to produce radiation for medical treatment purposes ("radiation devices");

receive location data for medical equipment items used for the medical procedures which scatter radiation produced by the radiation devices ("radiation scattering items");

receive location data for the number of AR tracking devices continuously or periodically throughout the medical procedures, wherein each location measurement provided by said location data is associated with a time;

receive data from said radiation devices indicating each time radiation is produced by a respective one of said radiation devices and a radiation scatter intensity field encountered at each of said one or more instances based on at least a type of said respective one of said radiation devices and a position of said respective one of said radiation devices relative to a respective one of said radiation scattering items when said respective one of said radiation devices is activated;

determine, by way of said one or more analytical subsystems, an estimated cumulative exposure level for each of the individuals during each of the medical procedures based on the location measurements for the individuals within the radiation scatter intensity fields at each of the instances each of the radiation devices are activated;

store each of said estimated cumulative exposure levels at said one or more databases in association with identifying information for an associated one of the individuals and a procedure code for an associated one of the medical procedures to build a data set;

develop, by way of said one or more analytical subsystems, average exposure level benchmarks for each of said medical procedures;

compare a particular one of the estimated cumulative exposure levels of a particular one of the individuals for a particular one of the medical procedures to a respective one of the benchmarks associated with the particular one of the medical procedures; and if the particular one of the estimated cumulative exposure levels for the particular one of the individuals exceeds the respective one of the benchmarks by at least a predetermined amount:

provide, by way of the notification subsystem of a particular one of the one or more intervention subsystems, an electronic notification at a particular one of the AR tracking devices associated with the particular one of the individuals, alerting the individual wearing the AR tracking device regarding the exceeded benchmark; and display, by way of the particular one of the one or more intervention subsystems, an intervention comprising suggested educational or training materials retrieved from said one or more reference databases at the particular one of the AR tracking devices or a prompt to initiate a videoconference with another one of the AR tracking devices associated with a similarly situated one of the individuals having more experience than the individuals associated with the particular one of the AR tracking devices.

23. A system for monitoring progress of a medical procedure by estimated radiation exposure, said system comprising:

one or more tracking devices, each associated with one of a number of individuals assisting with performance of the medical procedure and configured to track positions of the individuals within a medical facility where the medical procedure is performed;

a controller in electronic communication with each of the tracking devices and comprising executable software instructions stored at one or more electronic storage devices, which when executed, configure one or more processors to:

determine one or more relative locations of a medical equipment item used during the medical procedure which is configured to produce radiation for medical treatment purposes ("radiation device") and a medical equipment item known to scatter radiation produced by the radiation device ("radiation scattering item");

receive position data from the tracking devices during the medical procedure;

receive data indicating one or more instances radiation is produced by said radiation device to develop a radiation scatter intensity field at each of said one or more instances based on said relative locations; and determine an estimated exposure level for each of the individuals based on the positions of the individuals relative to the radiation scatter intensity field at each of the instances the radiation device is activated.

* * * * *